United States Patent [19]

Blum et al.

[11] Patent Number: 5,610,050
[45] Date of Patent: Mar. 11, 1997

[54] METHODS OF PREVENTING VIRAL REPLICATION

[75] Inventors: Hubert E. Blum, Zurich, Switzerland; Tsanyang Liang, Brookline, Mass.; Eithan Galun, Jerusalem, Israel; Jack R. Wands, Waban, Mass.

[73] Assignee: The General Hospital Corporation, Boston, Mass.

[21] Appl. No.: 51,935

[22] Filed: Apr. 23, 1993

Related U.S. Application Data

[63] Continuation-in-part of Ser. No. 846,328, Mar. 5, 1992, abandoned, which is a continuation-in-part of Ser. No. 511,428, Apr. 20, 1990, abandoned.

[51] Int. Cl.$^6$ ............................ C12N 7/06; C07H 21/04
[52] U.S. Cl. .................. 435/238; 435/172.3; 435/320.1; 536/23.1; 536/23.72; 536/24.5; 935/8; 935/34
[58] Field of Search .......................... 514/44; 435/172.1, 435/320.1, 238; 536/23.1, 23.72, 24.5; 935/8, 34; 800/DIG. 2

[56] References Cited

U.S. PATENT DOCUMENTS

| | | | |
|---|---|---|---|
| 4,689,320 | 8/1987 | Kaji | 514/44 |
| 4,757,055 | 7/1988 | Miller et al. | 514/44 |
| 4,806,463 | 2/1989 | Goodchild et al. | 435/5 |
| 5,004,810 | 4/1991 | Draper | 536/27 |
| 5,023,243 | 6/1991 | Tullis | 514/44 |
| 5,110,802 | 5/1992 | Cantin et al. | 514/44 |

FOREIGN PATENT DOCUMENTS

| | | |
|---|---|---|
| 28862/92 | 7/1993 | Australia. |
| 0180012 | 7/1986 | European Pat. Off.. |
| 0218474 | 4/1987 | European Pat. Off.. |
| 0331939 | 9/1988 | European Pat. Off.. |
| 0318215A1 | 5/1989 | European Pat. Off.. |
| WO86/05516 | 9/1986 | WIPO. |
| WO90/02176 | 3/1990 | WIPO. |
| WO91/16420 | 10/1991 | WIPO. |

OTHER PUBLICATIONS

R Weiss (1991) Science News 139:108–109.
C A Stein et al (1993) Science 261:1004–1012.
R Bartenschlager et al (1988) EMBO J 7:4185–4192.
M Nassal et al (1987) Arzneim–Forsch 37:748–751.
Wu and Wu, Specific Inhibition of Hepatitis B Viral Gene Expression in Vitro by Targeted Antisense Oligonucleotides, J. Biol. Chem. 267:12436–12439, 1992.
PCT Search Report from corresponding PCT Application No. PCT/US94/04559, mailed Jun. 24, 1994.
ER Kern (1990) Antiviral Agents and Viral Diseases of Man, 3rd ed., GJ Galasso et al, eds, pp. 94–95.
Blum et al., Latent Hepatitis B Virus Infection with Full–Length Viral Genome in a Patient Serologically Immune to Hepatitis B Virus Infection, Liver 8:307–318, 1988.
Coleman et al., A Novel Immune System Against Bacteriophage Infection Using Complementary RNA (micRNA), Nature 315:601–603, 1985.
Gendelman et al., Molecular Characterization of a Polymerase Mutant Human Immunodeficiency Virus, Virology 180:323–329, 1987.
Higuchi, Using PCR to Engineer DNA, PCT Technology (Henry A. Erlich, ed.) M Stockton Pres, New York, pp. 61–70, 1989.
Hirsch et al., Polymerase Gene Products of Hepatitis B Viruses are Required for Genomic RNA Packaging as Well as for Reverse Transcription, Nature 344:552–555, 1990.

(List continued on next page.)

*Primary Examiner*—Bruce R. Campell
*Attorney, Agent, or Firm*—Fish & Richardson P.C.

[57] ABSTRACT

The invention relates to methods and compositions for inhibition of viral replication. In particular, termination of replication of hepatitis B virus is achieved by introducing into a target cell an antisense oligonucleotide having a sequence substantially complementary to an mRNA which is in turn complementary to a portion of the minus strand of a hepatitis viral genome, which portion encoding solely part or all of the terminal protein region of the viral polymerase.

26 Claims, 13 Drawing Sheets

OTHER PUBLICATIONS

Inokuchi et al. Interference with Viral Infection by Defective RNA Replicase, J. Virology 61:3946–3949, 1987.

Blum et al., Naturally Occurring Missense Mutation in the Polymerase Gene Terminating Hepatitis B Virus Replication, J. Virology 65:1836–1842, 1991.

Blum et al., Inhibition of hepatitis B virus by antisense oligodeoxynucleotides, The Lancet 337:1230, 1991.

Cullen and Greene, Regulatory Pathways Governing HIV–1 Replication, Cell 58:423–426, 1989.

Grandgenett and Mumm, Unraveling Retrovirus Integration, Cell 60:3–4, 1990.

Hirsch et al., Polymerase Gene Products of Hepatitis B Viruses are Required for Genomic RNA Packaging as Well as for Reverse Transcription, Nature 344:552–555, 1990.

Hirsch et al., Replication of Duck Hepatitis B Virus in Two Differentiated Human Hepatoma Cell Lines After Transfection with Cloned Viral, DNA, Virology 167:136–142, 1988.

Izant and Weintraub, Constitutive and Conditional Suppression of Exogenous and Endogenous Genes by Anti–Sense RNA, Science 229:345–352, 1985.

Khudyakov and Makhov, Prediction of Terminal Protein and Ribonuclease H Domains in the Gene P Product of Hepadnaviruses, FEBS Letters 243:115–118, 1989.

Kim and Wold, Stable Reduction of Thymidine Kinase Activity in Cells Expressing High Levels of Anti–Sense RNA, Cell 42:129–138, 1985.

Melton, Injected anti–sense RNAs specifically block messenger RNA translation in vivo, Proc. Natl. Acad. Sci. USA 82:144–148, 1985.

Nakabayashi et al., Growth of Human Hepatoma Cell Lines with Differentiated Functions in Chemically Defined Medium, Cancer Research 42:3858–3863, 1982.

Okamoto et al., Typing Hepatitis B Virus by Homology in Nucleotide Sequence: Comparison of Surface Antigen Subtypes, J. Gen. Virol. 69:2575–2583, 1988.

Okayama and Berg, A cDNA Cloning Vector That Permits Expression of cDNA Inserts in Mammalian Cells, Molecular and Cellular Biology 3:280–289, 1983.

Preiss et al., Molecular Genetics of Kruppel, a gene required for segmentation of the Drosophila embryo, Nature 313:27–32, 1985.

Rosenberg et al., Production of Phenocopies by Kruppel antisense RNA injection into Drosophila embryos, Nature 313:703–706, 1985.

Ratner et al., Complete nucleotise sequence of the AIDS virus, HTLV–III, Nature 313:277–284, 1985.

Saiki et al., Primer–Directed Enzymatic Amplication of DNA with a Thermostable DNA Polymerase, Science 239:487–491, 1988.

Sarver et al., Ribozymes as Potential Anti–HIV–1 Therapeutic Agents, Science 247:1222–1225, 1990.

Seeger et al., Biochemical and Genetic Evidence for the Hepatitis B Virus Replication Strategy, Science 232:477–484, 1986.

Traktman et al., Molecular Genetic Analysis of Vaccinia Virus DNA Polymerase Mutants, J. Virology 63:841–846, 1989.

Schlicht et al., Synthesis and Encapsidation of Duck Hepatitis B Virus Reverse Transcriptase Do Not Require Formation of Core–Polymerase Fusion Proteins, Cell 56:85–92, 1989.

Varmus, Retroviruses, Science 240:14271435, 1988.

Will et al., Replication Strategy of Human Hepatitis B Virus, J. Virology 61:904–911, 1987.

Xian–Jun et al., Tissue–Specific Activity of Heterologous Viral Promoters in Primary Rat Hepatocytes and Hep G2 Cells, Hepatology 10:781–787, 1989.

von Ruden et al., Inhibition of Human T–Cell Leukemia Virus Type I Replication in Primary Human T Cells that Express Antisense RNA, J. Virology 63:677–682, 1989.

Ganem et al., The Molecular Biology of The Hepatitis B Viruses, Ann. Rev. Biochem. 56:651–93, 1987.

Offensperger, W., et al., "In Vivo Inhibiton of Duck Hepatitis B Virus Replication and Gene Expression By Phosphorothioate Modified Antisense Oligodeoxynucleotides", 1993, *EMBO J.,* 12(3):1257–62.

Wang, G. H., et al., "The Reverse Transcriptase of Hepatitis B Virus Acts As a Protein Primer for Viral DNA Synthesis", 1992, *Cell,* 71:663–70.

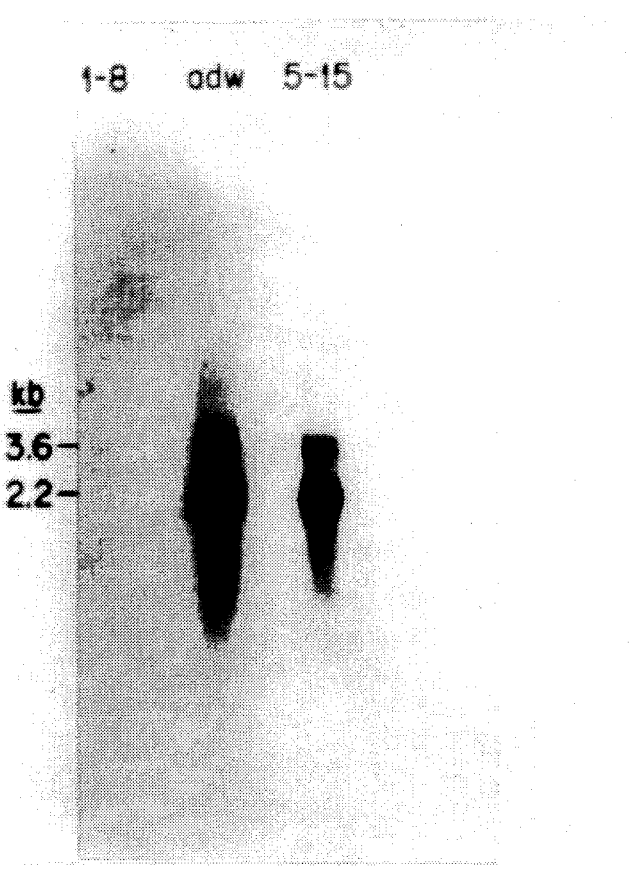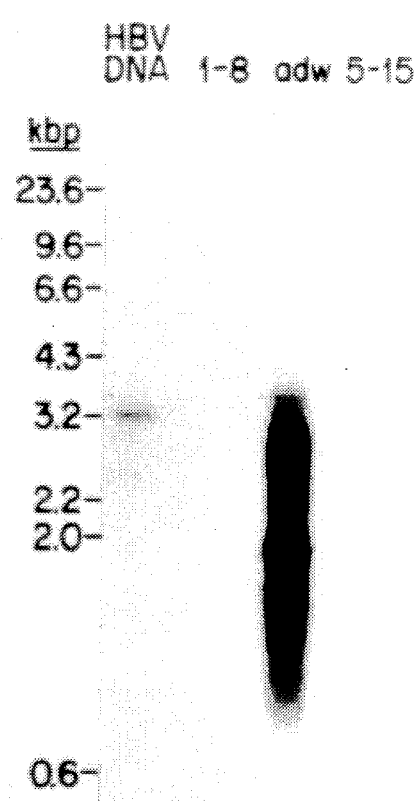
FIG. 1
FIG. 2

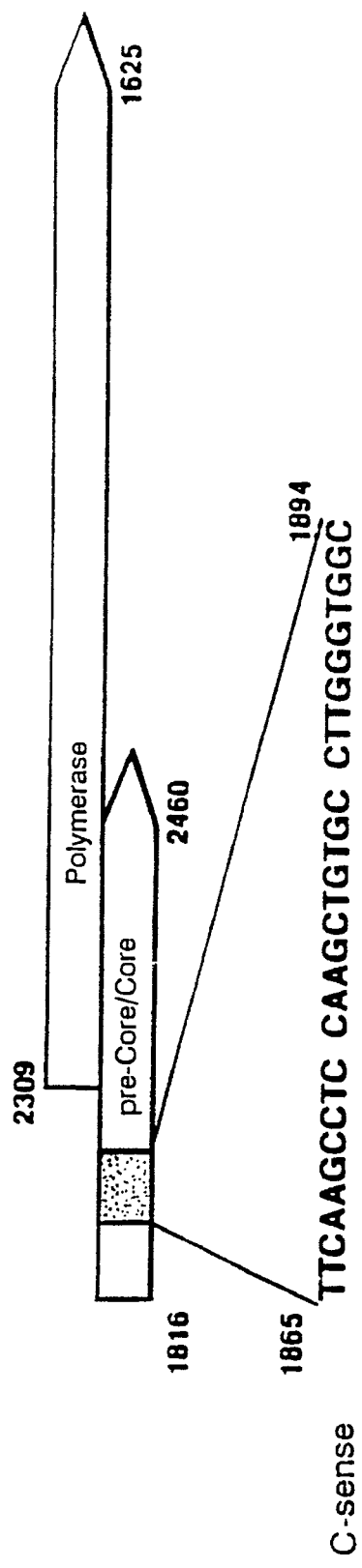
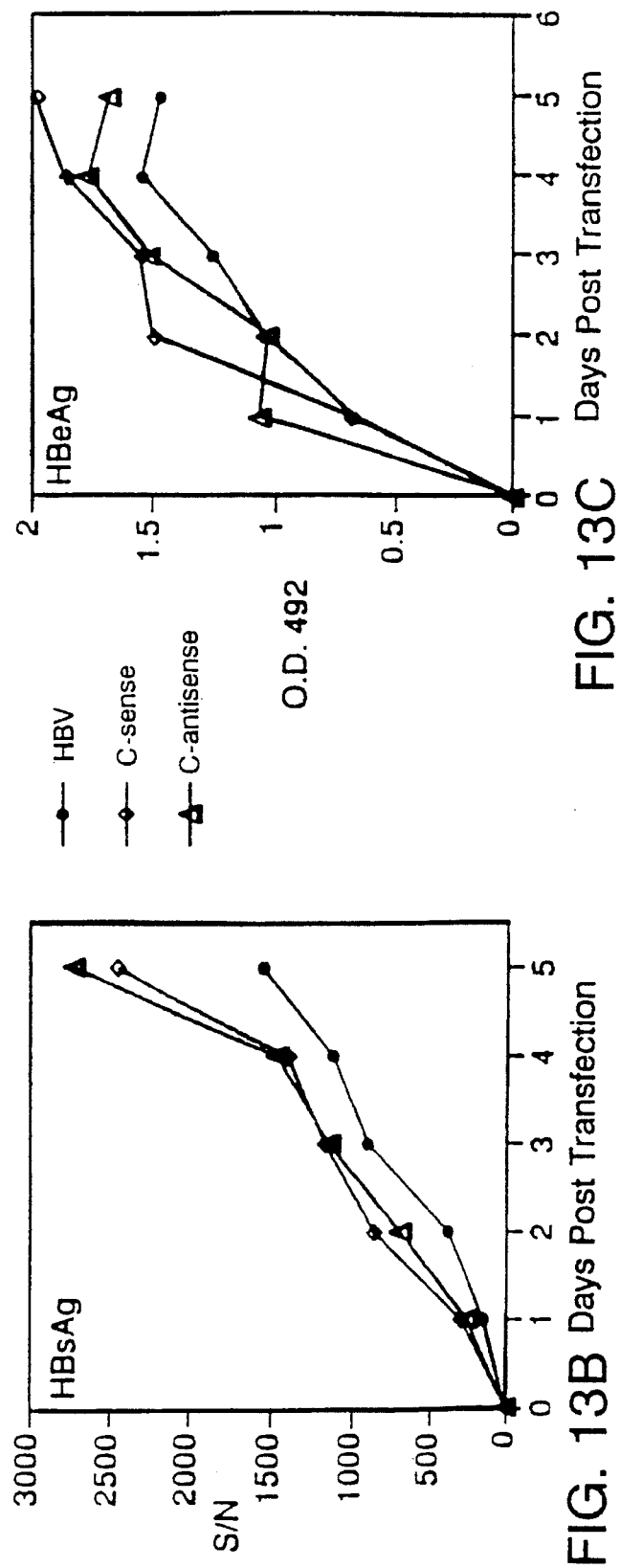
FIG. 13A
FIG. 13B
FIG. 13C

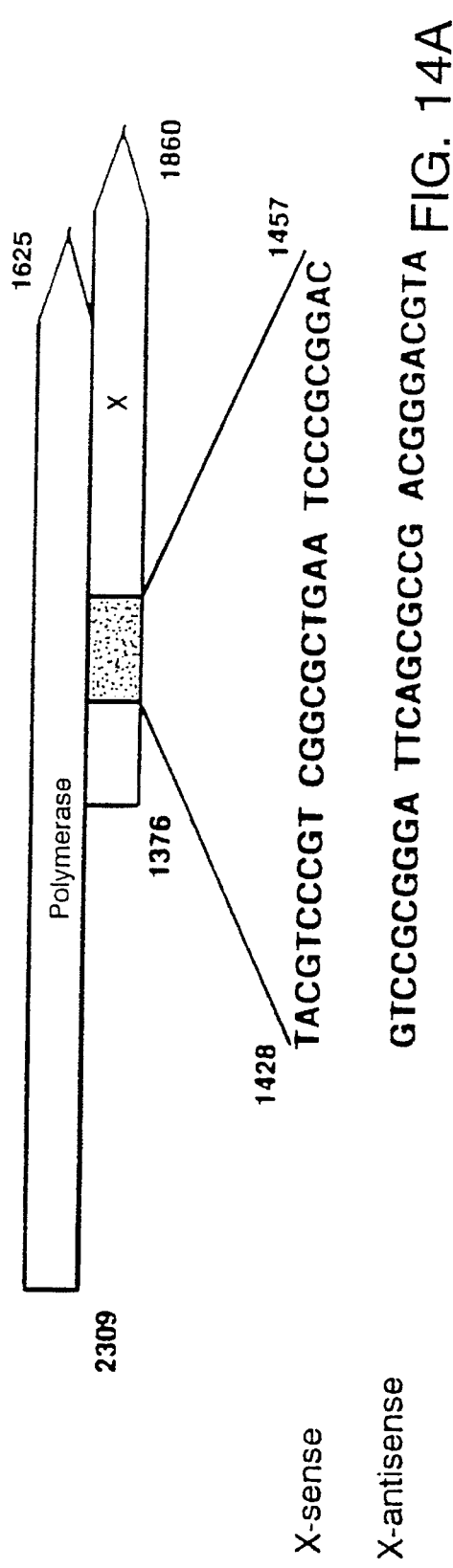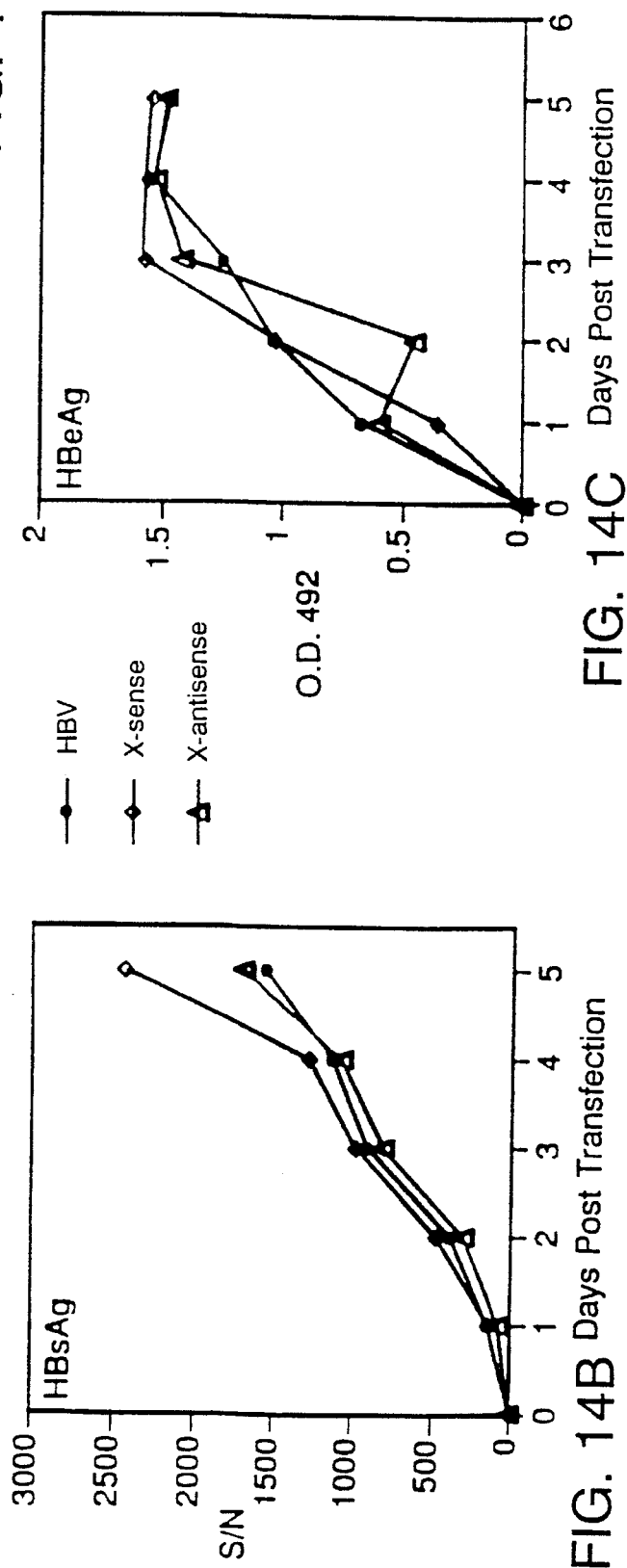

METHODS OF PREVENTING VIRAL REPLICATION

This invention was made with support from the United States Government under grant CA-35711 from the National Institutes of Health. The Government may have certain rights in this invention.

This application is a continuation-in-part of application Ser. No. 07/846,328, filed Mar. 5, 1992, now abandoned which is a continuation-in-part of application Ser. No. 07/511,428, filed Apr. 20, 1990, now abandoned, both of which are incorporated herein by reference.

The invention relates to antiviral oligonucleotide compositions, pharmaceutical compositions containing such oligonucleotides, and their use for the prevention and treatment of viral diseases.

BACKGROUND OF THE INVENTION

The consequences of a viral infection depend upon a number of factors, both viral and host. These factors which affect pathogenesis include the number of infecting viral particles and their path to susceptible cells, the speed of viral multiplication and spread, the effect of the virus on cell functions, the host's secondary responses to the cellular injury, and the immunologic and non-specific defenses of the host. In general, the effects of viral infection include acute and chronic clinical diseases, asymptomatic infections, induction of various cancers, and chronic progressive neurological disorders. Viruses are potent infectious pathogenic agents because virions produced in one cell can invade other cells and thus cause a spreading infection. Viruses cause important functional alterations of the invaded cells, often resulting in cellular death.

Viral infections continue to be a major medical problem throughout the world. For example, acute and chronic hepatitis virus infection and its sequelae present a major problem. In fact, approximately 5% of the world's population, probably at least 400 million people in the world today, are infected with the hepatitis B virus (HBV). HBV presents a high risk of acute fulminant hepatitis as well as chronic liver disease, including cirrhosis, chronic active hepatitis, and the eventual development of primary hepatocellular carcinoma in individuals who remain chronic carriers of the virus.

The dramatic effects of the human immunodeficiency virus (HIV) provide another illustration of the results of viral disease. There are currently more than 27,700 diagnosed cases of AIDS in the United States, and the U.S. Public Health Service predicts that by the end of 1991 more than 179,000 persons will have the disease. Thus, intense medical research is being devoted to the development of diagnostic tools and vaccines to counter HIV. AIDS and hepatitis represent only two of the diseases wrought by viral infection.

Therapeutic studies during the last ten years have identified promising drugs with antiviral effects, including the nucleotide analog adenine arabinoside (Ara-A), its more soluble monophosphate Ara-AMP, and Interferon-alpha. Although effective in some patients, such agents have been shown frequently to result in only a transient response or to have significant toxicity. Accordingly, there is a continuing need for methods and therapeutic agents to stop viral replication and prevent the spread of the virus to additional cells. However, this goal presents considerable difficulties. A major problem is that of inhibiting the virus without harming the host cells. The dependence of viral multiplication on cellular genes limits the points of differential attack. Even the largest viruses have fewer biochemical reactions that are unique in relation to the cells of the host. Further, it is only after extensive viral multiplication and cellular alteration have occurred that viral infections become evident. Therefore, the most feasible approach to control viral infection is prophylaxis. Therapy in most cases is limited to situations where the killing of some uninfected cells can be tolerated if the damage is subsequently repaired.

Another important limitation of antiviral therapy is the emergence of resistant mutants. In order to avoid their selection, the principles valid for bacteria are equally applicable to viruses: adequate dosage, multi-drug treatment, and avoiding therapy unless clearly indicated. Therefore, because of the serious nature of viral infection and the obstacles presented by the nature of the infecting virus, there is an urgent need for methods which control viral replication. A method which would be applicable to RNA and DNA viruses would have widespread applicability.

Synthetic antisense oligonucleotides have been used as inhibitors of viral gene expression. Smith et al., *Proc. Natl. Acad. Sci. USA*, 2787–2791 (1986), report antiviral activity of an oligo(nucleoside methylphosphonate) complementary to the splice junction of herpes simplex virus type I immediate early pre-mRNAs 4 and 5. See also: Agris et al., Inhibition of vesicular stomatitis virus protein synthesis and infection by methylphosphonates, Biochem. 25, 6268–6275 (1986); Zamecnik et al., Inhibition of Rous sarcoma virus replication and cell transformation by a specific oligodeoxynucleotide, *Proc. Natl. Acad. Sci. USA* 75:280–284 (1978); and Zamecnik et al., Inhibition of replication and expression of human T-cell lymphotropic virus type III in cultured cells by exogenous synthetic oligonucleotides complementary to viral RNA, *Proc. Natl. Acad. Sci. USA* 83, 4143–4146 (1986). Goodarzi et al., *J. Gen. Virol.* 71:3021–3025 (1990), report inhibition of expression of the gene for hepatitis B virus surface antigen by antisense oligodeoxynucleotides directed at the cap site of mRNA and regions of the translational initiation site of the HBsAg gene.

SUMMARY OF THE INVENTION

The invention relates to antisense oligonucleotides, preferably antisense oligodeoxynucleotides, as antiviral agents against HBV; pharmaceutical compositions providing such antiviral oligonucleotides; and methods for their use in inhibiting HBV. Antisense oligonucleotide compositions complementary to a region of RNA encoded by the HBV polymerase gene completely block viral transcription, antigen production, and replication. Preferred are antiviral oligonucleotides substantially complementary to RNA encoding a region of the terminal protein domain of the HBV polymerase protein. Preferred is such an antiviral oligonucleotide comprising at least about 12 nucleotides corresponding to a sequence of nucleotides from about n.t.s. 2850 to about n.t.s. 2794, more preferably from about n.t.s. 2833 to about n.t.s. 2794, of HBV subtype adw2, numbering according to the sequence published in Blum et al., Persistence of Hepatitis B Viral DNA After Serological Recovery from Hepatitis B Virus Infection, *Hepatology* 14, No. 1:56–63 (1991). The sequence of the (+) strand from n.t.s. 2357 to n.t.s. 3172 is as shown in SEQ ID NO. 49. Such antiviral oligonucleotides can be provided to the target cell either exogenously as an antisense DNA or RNA, or by insertion of a sense DNA sequence into an expression vector capable of producing the antisense oligonucleotides endogenously within the target cell.

The invention also relates to methods of complete and irreversible termination of replication of a viral polymerase-containing virus achieved by introducing at least one mutation at specific regions in the viral polymerase gene. The mutant gene or gene products (DNA, RNA, or protein) can be supplied to the virus-infected cell to effect defective replication. The method is useful for the prevention and treatment of viral diseases. Both DNA and RNA viruses which utilize polymerase gene products for replication can be inhibited by the disclosed method.

BRIEF DESCRIPTION OF THE DRAWINGS

FIG. 1: Mutant HBV genome 5-15 is efficiently transcribed in HuH 7 hepatoma cells. HuH 7 cells (Nakabayashi, H. et al., Cancer Res. 42:3858–3863 (1982)) were grown in MEM medium supplemented with 10% FBS. At about 90% confluence the cells were transfected with 20 ug of cloned DNA per 100 mm dish, using the calcium phosphate method (Chen, C. et al., Mol. Cell. Biol. 7:2745–2752 (1987)). HBV DNAs used were the incomplete genome 1-8 (negative control; see Table I), a head-to-tail dimer of 'wild-type' adw and a head-to-tail dimer of the mutant viral genome 5-15. Forty-eight hours after transfection, total RNA was prepared from cells by the guanidine isothiocyanate method (Sambrook, J. et al., Molecular cloning: A laboratory manual, 2nd Edition, Cold Spring Harbor, N.Y., Cold Spring Harbor Laboratory Press (1989)), fractionated by formaldehyde 1.25% agarose gel electrophoresis, transferred to a Nytran membrane (Schleicher & Schuell, Keene, N. H.) and hybridized with a full-length HBV DNA probe, $^{32}$P-labeled by nick translation. Autoradiographic exposure at −80° C. was 12 hours.

FIG. 2: Mutant HBV genome 5-15 is replication defective. HuH 7 cells were grown and transfected as described above for FIG. 1. Five days after transfection, cell culture media were collected and cells: were lysed in NP40 (Hirsch, 5 R. et al., Virology 167:136–142 (1988)). The cell lysate was centrifuged for 30 minutes at 50,000×g (20° C.). To the supernatant, DNase I (1 ug per ml; Worthington) was added in order to digest input DNA. The solution was layered in a sucrose cushion (30% sucrose, 20 mM Tris-HCl, pH 7.4, 100 mM NaCl, 0.1% 2-mercaptoethanol, 0.1% bovine serum albumin) and centrifuged for 12 hours at 178,000×g (4° C.). The pellet was digested for 3 hours at 55° C. with proteinase K (500 ug/ml) in the presence of 20 mM Tris-HCl, pH 8, 10 mM EDTA, 1% SDS. After phenol extraction, nucleic acids were precipitated with ethanol. After lyophilization, the precipitate was dissolved in 10 mM Tris-HCl, pH 7.4, 1 mM EDTA, and 1 ug DNase-free RNase A per ml, fractionated by 1.25% agarose gel electrophoresis, transferred to a Nytran membrane and hybridized to a full-length HBV DNA probe, $^{32}$P-labeled by nick translation. Cytoplasmic DNA from one 100 mm dish was applied per lane. Autoradiographic exposure at −80° C. was 4 hours.

FIG. 13A: Schematic illustration of the sense and antisense oligonucleotides derived from the core gene region of the HBV genome.

FIGS. 13B and 13C: Effect of sense and antisense oligonucleotides derived from conserved sequences of the HBV core gene region on HBsAg (B) and HBeAg (C) synthesis and secretion. The core-region derived oligonucleotides exhibited no effect on the levels of these two viral proteins.

FIG. 14A: Schematic illustration of the sense and antisense oligonucleotides derived from the X region of the HBV genome.

FIGS. 14B and 14C: Effect of sense and antisense oligodeoxynucleotides derived from conserved sequences of the HBV X region on HBsAg (B) and HBeAg (C) expression. The X-region-derived oligonucleotides exhibited no effect on the levels of these two viral proteins.

DETAILED DESCRIPTION

Figure 3:
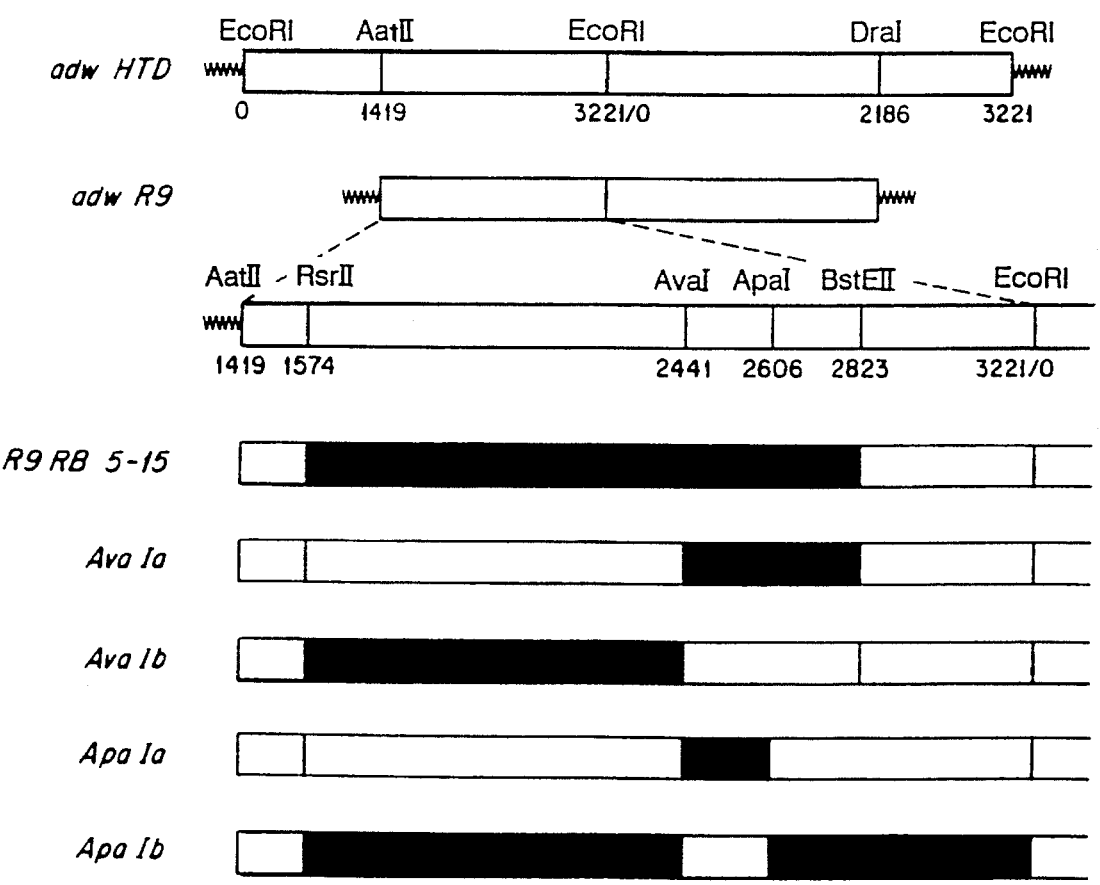
FIG. 3: DNA sequences responsible for replication-defectiveness of HBV mutant 5-15 map between nucleotide position 2606 (Apa I) and 2823 (Bst EII). The head-to-tail dimer of 'wild-type' adw2 (adw HTD, cloned into the Eco RI site of pGEM-7) was subcloned as Aat II (1419) and Dra I (2186) fragment to yield the truncated, replication-competent construct adw R9. By exchange of specific regions between adw R9 and the mutant HBV genome 5-15, the sub-clones illustrated were obtained. The regions in black indicate HBV 5-15 insertions into adw R9. The replication-competence of these constructs was analyzed as described in the legend to FIG. 2.

Human hepatitis B (HBV) is now recognized to be a member of a family of animal viruses called hepadnaviruses (hepatotropic DNA viruses). Human HBV is classified as a hepadnavirus type 1. Similar viruses infect other animal species, including woodchucks, ground and tree squirrels, Pekin duck, and heron, producing acute and chronic hepatitis as well as hepatocellular carcinoma. Full-length molecular clones of these hepadnaviruses have been obtained and their nucleotide sequences determined. The coding organization of the mammalian viruses is now known to be virtually identical to that of human HBV.

Replication strategy of the hepatitis B virus can be found in Seeger et al., Science 232:477–484 (1986); Khudyakov et al., FEBS Letters 243:115–118 (1989); Will et al., J. of Virol. 61:904–911 (1987); and Hirsch et al., Nature 344:552–555 (1990).

Retroviruses and retroviral integration is discussed in Varmus, H., Science 240:1427–1435 (1988); and Grandgenett et al., Cell 60:3–4 (1990).

The infectious HBV virions, called "Dane particles", are 43 nm double-shelled particles which include the outer coat of HBV surface antigen (HBsAg) containing a basic phosphoprotein of 21 kd, the HBV core antigen (HBcAg). Within the HBV nucleocapsid core is a predominantly double-stranded, but partially single stranded, DNA genome measuring 3200 base pairs, as well as an endogenous DNA polymerase which directs replication and repair of HBV DNA. The full-length strand of HBV DNA is complementary to the viral mRNAs and by convention is designated to be of minus polarity. The shorter complementary strand is designated the plus strand. While the 5' end of the plus strand is fixed, the position of the 3' end is variable, even within molecules of the same viral stock. In the endogenous polymerase reaction, the single-stranded gap is repaired by the addition of nucleotides to the 3' end of the plus strand DNA. A second asymmetry occurs at the 5' termini of the genomic molecule, where protein is covalently linked to the minus strand, whereas a 5' oligonucleotide is attached to the 5' end of the plus strand.

Replication of HBV proceeds via reverse transcription of an RNA intermediate using protein and RNA primers for the generation of the first and second DNA strands. Large sections of the genome are translated in more than one reading frame. Within a reading frame, proteins from multiple in-phase initiator codons are expressed from overlapping transcripts. The resulting closely related gene products can be post-translationally processed and assembled into a variety of structures of differing function or subcellular distribution.

Four major open reading frames (ORFs) encoded by the HBV minus strand have been identified and characterized: 1) the pre-S and S gene, which code for the HBsAg and several other less well characterized gene products; 2) the C gene, which codes for HBcAg and HBeAg; 3) the P gene, which codes for the viral DNA polymerase; and 4) the X gene, which codes for the transactivating X protein, HBx, seen more frequently in patients with hepatocellular carcinoma. Within the HBV polymerase gene is a region encoding the terminal protein domain of the polymerase protein, which encompasses the initial approximately 25% of the amino terminal end of the polymerase ORF, followed by a spacer region, the DNA polymerase and the RNAase H regions. The polymerase ORF of HBV subtype adw2 extends from about n.t.s. 2357 to about n.t.s. 1625, with the region coding for the terminal protein domain located from about n.t.s. 2357 to about n.t.s. 3172 (numbering as published in Blum et al., Persistence of Hepatitis B Viral DNA After Serological Recovery from Hepatitis B Virus Infection, Hepatology 14, No. 1:56–63 (1991)). The corresponding sequences for other strains or subtypes of HBV can be determined by those of skill in the art by aligning homologous sequences, e.g., by using sequence data available in GenBank®. For example, it was determined in this manner that the polymerase ORF of the HBV Hep strain is found from about n.t.s. 2357 to 1620. The nucleotide sequences of various hepatitis virus strains can be found in Okamoto et al., J. Gen. Virol. 69:2575–2583 (1988) and through GenBank. The teachings of these references is hereby incorporated by reference. The complete nucleotide sequence of HBV mutant 5-15, which exhibits closest homology with published sequences for HBsAg subtype adw2, is reported in Blum et al., Persistence of Hepatitis B Viral DNA After Serological Recovery from Hepatitis B Virus Infection, Hepatology 14, No. 1: 56–63, at 58 (1991), the teaching of which is incorporated herein by reference. See FIG. 7, which sets forth a map of the HBV viral genome, showing the organizational structure of the four major ORFs and the pregenomic and subgenomic RNA species.

A reverse transcriptase, a transcription product of the polymerase ORF, is involved in HBV replication via the pregenomic RNA stage. The structure and function of the polymerase open reading frame, including the terminal protein (TP) domain, is described by Wang et al., The Reverse Transcriptase of Hepatitis B Virus Acts As a Protein Primer for Viral DNA Synthesis, *Cell* 71:663–670 (1992), the teaching of which is hereby incorporated by reference.

Four major steps are believed to be fundamental to replication of hepadnavirus genomes:

1. completion of the single-stranded gap by the addition of nucleotides to the 3' end of the plus strand DNA, to form covalently closed circular DNA (cccDNA) within the nucleus of infected hepatocytes;

2. transcription of cccDNA by host RNA polymerase to generate an RNA template of plus strand polarity for reverse transcription, with encapsidation of the pre-genomic RNA into virus cores;

3. synthesis of the first (minus) strand of DNA by copying pregenomic RNA, using a protein primer (core associated reverse transcription); and 4. synthesis of the second (plus) strand of DNA by copying the first DNA strand and using an oligomer of viral RNA as primer, to form the mature viral genomic DNA. Amplification of the viral genome is believed to occur during synthesis of pregenomic RNA from cccDNA.

HBV viral RNA serves as both the template for synthesis of genomic DNA via reverse transcription, and the messenger RNA for synthesis of certain viral proteins. This is achieved by the synthesis of two classes of viral RNA, genomic and subgenomic. Whereas the genomic RNAs (3.5 kb in length) contain the complete viral genetic information, subgenomic RNAs of 2.1 and 2.4 kb in length are also transcribed. All of these RNAs are of plus strand polarity, unspliced, and polyadenylated at a common 3' terminus.

It has been determined that the antiviral oligomers of the invention which are complementary to part or all of a region of HBV RNA (mRNA/genomic RNA) encoding the HBV polymerase, preferably a region encoding a portion of the polymerase protein terminal protein domain, can totally block viral replication. "Antisense" describes the interaction of oligonucleotides (which can be RNA, DNA, or a combination thereof) with cellular nucleic acid targets in a sequence-specific manner, more particularly, the interaction of oligonucleotides (having the sequence of the HBV minus strand DNA) with their complementary HBV genomic RNA or mRNA, to inhibit HBV viral replication. The interaction of antisense oligonucleotides with their receptor sequences results from hybridization interactions. Antisense oligonucleotides inhibit viral replication, including inhibition of the production of the protein product, in this case, the HBV polymerase protein. The therapeutic applications of antisense oligonucleotides in general are described, e.g., in the following review articles: Le Doan et al., Antisense Oligonucleotides as Potential Antiviral and Anticancer Agents, *Bull. Cancer* 76:849–852 (1989); Dolnick, B. J., Antisense Agents in Pharmacology, *Biochem. Pharmacol.* 40:671–675 (1990); Crooke, *Annu. Rev. Pharmacol. Toxicol.* 32, 329–76 (1992).

The invention relates to a composition of matter consisting essentially of an antiviral antisense oligonucleotide of the invention, preferably an oligodeoxynucleotide, consisting of a sequence of at least 11 nucleotides (preferably at least 12, more preferably at least 15, and most preferably at least 18) substantially complementary to an RNA (e.g., messenger RNA or genomic RNA) which is complementary to a portion of the minus strand of a hepatitis viral genome, which portion encodes solely part or all of the terminal protein domain of the HBV polymerase. Because the antisense oligonucleotides are substantially complementary to their respective HBV RNA sequences, these complementary sequences can hybridize under physiological conditions, with resultant inhibition of viral replication. Antisense oligonucleotides of the invention have been shown to be capable of completely inhibiting HBV replication. Accordingly, the invention also relates to methods of inhibiting HBV replication in cells containing HBV, including methods of preventing HBV infection in an animal (e.g., a human or other mammal, or a bird) exposed to HBV, and methods of treating an animal infected with HBV. The invention also relates to pharmaceutical compositions for use in preventing HBV infection in an animal exposed to HBV, or treating an animal infected with HBV. Preferred are such pharmaceutical compositions formulated for parenteral administration. Such pharmaceutical compositions will contain an effective antiviral amount of an oligonucleotide of the invention and a pharmaceutically acceptable carrier.

The invention also relates to a composition of matter consisting essentially of at least one antiviral antisense oligonucleotide substantially complementary to an RNA sequence (mRNA or pregenomic RNA) encoded by a portion of the terminal protein region of the polymerase gene of HBV, preferably corresponding to a sequence from about n.t.s. 2598 to about n.t.s. 2998 of HBV subtype adw2, more preferably corresponding to a sequence from about n.t.s. 2698 to about n.t.s. 2898 of HBV subtype adw2, even more preferably an oligonucleotide comprising at least about 12 nucleotides, and preferably at least 15 nucleotides, corresponding to a sequence of nucleotides from about n.t.s. 2794 to about 2850 or 2833 of HBV subtype adw2. The antisense oligonucleotide is preferably less than about 400 nucleotides in length, more preferably less than about 250 nucleotides in length, even more preferably less than about 100 nucleotides in length, and most preferably less than about 50 nucleotides in length (e.g., 20, 30 or 40). Corresponding sequences for strains of HBV other than HBV subtype adw2, e.g., the strains listed in Table 1, infra, as well as other strains of HBV that have been and will in the future be isolated and sequenced, can be determined by those of ordinary skill in the art by aligning sequences for homology, e.g., by using an available database such as GenBank.

It has been found that antisense oligonucleotides containing most or all of the sequence ACCCGCAAAAT (SEQ ID NO: 38) (e.g., at least eight of the eleven nucleotides, preferably a contiguous segment of at least eight, and more preferably at least nine; even more preferably at least ten; and most preferably all eleven) are particularly useful in the methods of the invention. (Although written as a DNA sequence, such sequence is herein understood to include the RNA equivalent as well.) Such oligonucleotides may include additional sequence which is or is not complementary to the target RNA. In preferred embodiments, the antisense oligonucleotide contains at least two additional nucleotides immediately 5' to the 11-mer sequence, at least one of which nucleotides is a thymidine (or uridine). For example, the antisense oligonucleotide could consist of a 12 to 40 (preferably 15 to 30) nucleotide long segment of the sequence identified herein as ATC-40: ATA TGG TGA CCC GCA AAA TGA TGC GCT ACG TGT GGG TTC C (SEQ ID NO: 11).

Antisense oligonucleotides of the invention can be supplied to a target cell either exogenously as DNA or RNA, or endogenously, by supplying a DNA sequence from which the desired antisense oligonucleotide may be expressed by the target cell. In the latter case, the DNA to be expressed may be supplied to the target cell, preferably a hepatocyte, as a recombinant nucleic acid (e.g., a DNA molecule) containing a sequence complementary to an antisense RNA (aRNA), which in turn is substantially complementary to HBV polymerase-encoding mRNA, wherein expression of said aRNA is capable of inhibiting viral replication in a cell host to said molecule. This nucleic acid is characterized in that it (a) is capable of being replicated in a hepatocyte under conditions that normally prevail within the hepatocyte, and (b) is transcribed in a hepatocyte to produce an antisense oligoribonucleotide of at least 12 nucleotides substantially complementary to an RNA complementary to a portion of the minus strand of a hepatitis viral genome, which portion encodes solely part or all of the terminal protein region of the viral polymerase. The sequence transcribed into the antisense RNA is preferably operatively linked to a cell specific promoter to direct expression in the hepatocyte. The invention also includes a method for inhibiting hepatitis B viral replication in a cell by introducing the antiviral oligonucleotide into the cell, which may be accomplished by introducing the antisense molecule itself directly into the cell, or by introducing into the cell the nucleic acid which is transcribed within the cell to produce multiple copies of the antisense oligonucleotide as an oligoribonucleotide.

DESCRIPTION OF SPECIFIC EMBODIMENTS

Methods and compositions are provided for the termination of viral replication. In one embodiment such methods involve a defective form of a protein which is necessary for initiation of the polymerase reaction. Specific changes may be introduced into the polymerase gene region which encodes the necessary protein. The mutation leads to complete and irreversible termination of replication of the virus. Further, by supplying the defective protein to a virus, normal viral replication may be interrupted.

The mutation is introduced or inserted into a region of the polymerase gene resulting in the production of a defective protein. Without being bound by any specific theory, it is hypothesized that the protein to be mutagenized is necessary for viral replication by serving as a primer for replication. The defective protein, however, is unable to prime transcription by RNA and DNA polymerases. Alternatively, the defective protein may not allow encapsidation of pregenomic RNA (Hirsch et al., Nature 344:552–555 (1990)). It is noted that the method of inhibition may involve another aspect of viral replication, and thus patentability is not predicated on any proposed mechanism.

While the precise details of viral replication vary from virus to virus, certain aspects of the mechanism are shared. For example, RNA-directed DNA synthesis, first described for retroviruses, is now recognized as the probable means for the transfer of genetic information in various other settings, including the replication of hepatitis and cauliflower mosaic viruses. Such RNA-directed DNA synthesis commonly involves the synthesis of a strand of DNA from a single-stranded RNA template and a second DNA strand from the first; primers for each of the two strands; and a means for removing the RNA template after reverse transcription, to allow synthesis of the second DNA strand.

For purposes of the present invention, attention is focused on the role of the polymerase gene products in viral replication. The introduction of specific changes into the polymerase gene can effectively terminate replication of the virus. The methods are therefore applicable to both RNA and DNA viruses, particularly those viruses which use polymerase gene products to prime transcription for RNA and DNA polymerases. Viruses subject to the disclosed methods include hepadnaviruses, such as hepatitis viruses, retroviruses such as HIV, adenoviruses, herpes viruses, pox viruses, picornaviruses, orthomyxoviruses, paramyxoviruses, coronaviruses, pestiviruses, flaviviruses, and the like.

The methods involve the introduction of a mutation into a region of the polymerase gene. By "introduction of a mutation" is intended the substitution, deletion, or addition, preferably the substitution of nucleotide(s) in the gene. The region for insertion of the mutation may be identified by a comparison of the conserved amino acid positions in the polymerase genes or gene products of various strains of the virus. For example, when the polymerase genes of various HBV strains were compared, the amino acid position 164 was found to be highly conserved (see Table 1). When a single point mutation was introduced at nucleotide 2798, which corresponds to residue 164, a defective protein was produced which interrupted viral replication.

In the same manner, polymerase gene regions of other viruses can be scrutinized for critical amino acid positions. Mutations can be inserted into these positions and the resulting gene product tested for an effect on viral replication.

An alternative strategy is to introduce mutations into RNA and DNA viruses randomly in the polymerase gene. The proteins resulting from such changes are then tested for their effect on viral DNA replication.

From the work with hepatitis B virus, the mechanism of termination of viral replication may involve the defective production of a protein necessary for initiation of the polymerase reaction. This protein serves as a primer for the reverse transcription of the minus strand of DNA, which is an important step in the replication life cycle of all hepadnaviruses. This indicates that mutations can be introduced into the protein necessary for initiation of the polymerase reaction to inhibit viral replication. For hepadnaviruses, this includes .introducing mutations into the pregenomic RNA and for priming the reverse transcription of the minus strand DNA.

For retroviruses, second strand synthesis is primed by a viral RNA oligomer that is produced from a polypurine region by a ribonuclease activity associated with the reverse transcriptase and specific for RNA-DNA hybrids, ribonuclease H (RNAase H). Ribonuclease H is a protein product of the retroviral polymerase gene. Accordingly, the RNAase H gene region may be mutated by site-specific mutagenesis followed by testing of the effect of the defective protein products on viral replication.

Methods for mutagenesis are well known in the art. In particular, with site-specific mutagenesis techniques, nearly any amino acid position in a target protein can be manipulated at will. See Smith, M., *Ann. Rev. Genet.* 19: 423 (1985), herein incorporated be reference. See also, Higuchi, R., *Using PCR to Engineer DNA,* p. 61–70, In H. A. Erlich (ed.) PCR Technology, Stockton Press, New York (1989).

Another means for inserting mutations into the polymerase gene is to construct nucleic acid segments of the polymerase gene, using known methods for nucleic acid synthesis. See generally, *Synthesis and Applications of DNA and RNA,* Narang, S., Ed., Academic Press (1987), and the references cited therein. Thus, in those instances where the nucleic acid sequence of the virus or at least the polymerase gene of the virus is known, synthetic constructs can be made. The synthetic constructs will contain mutations or changes from the natural sequence at specific sites. The expressed protein can then be tested for its effect upon viral replication.

Nucleotide sequences of several viral genomes are published. For example, the nucleotide sequence of the HIV can be found in Ratner et al., *Nature* 313:277–284 (1985). The nucleotide sequence of the hepatitis virus can be found in Okamoto et al., *J. Gen. Virol.* 69:2575–2583 (1988) and is available through GenBank.

After mutagenesis of the identified target polymerase gene region, the effect of the mutation on viral replication can be tested. Viral replication can be assayed by determining the presence of replication products or viral transcripts. In this manner, cell lysates and cell culture media can be analyzed for the presence of viral transcripts, proteins, and replicative forms of viral DNA. To detect virus-specific transcripts, viral-encoded proteins may be identified by solid-phase radioimmunoassay, both in cell lysates and culture media. Specifically, the replication competence of a mutant viral genome may be assessed by Southern blot hybridization of cytoplasmic DNA after transfection of cells with the mutant virus. See experimental section for more details. Also, details on hybridization can be found in *Nucleic Acid Hybridization, A Practical Approach,* IRL Press, Washington, D.C. (1985).

Once a particular mutant protein is identified it can be used to terminate viral replication in a number of ways. The mutation can be supplied at the DNA, RNA or protein level. A more attractive approach is to provide for expression of the protein in a host cell infected with the virus or susceptible to viral infection. In this manner, the mutated polymerase gene or gene region can be placed in a vector which is capable of transforming the host cells. The gene is placed downstream from a suitable promoter which provides for tissue-specific or general expression. In the case of hepatitis, the viral DNA is placed downstream from a liver-specific promoter to induce expression in the liver. For other viruses, constitutive promoters can be utilized.

For expression in a host cell, the mutant gene can be operably linked into an expression vector and introduced into a host cell to permit expression of the defective protein by that cell. The gene with the appropriate regulatory regions will be provided in proper orientation and reading frame to allow for expression. Methods for gene construction are known in the art. See in particular, *Molecular Cloning, A Laboratory Manual,* Sambrook et al., eds., Cold Spring Harbor Laboratory, 2nd Edition, Cold Spring Harbor, N.Y. (1989).

A wide variety of transcriptional and translational regulatory sequences may be employed. The signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed.

The expression of the mutant viral DNA in eukaryotic hosts requires the use of eukaryotic regulatory regions. Such regions will, in general, include a promoter region sufficient to direct the initiation of RNA synthesis. Typical promoters include the promoter of the mouse metallothionine I gene (Hammer, D. et al., *J. Mol. Appl. Gen.* 1:273–288 (1982)); the Tk promoter of herpes virus (McKnight, S., *Cell* 31:355–365 (1982)); the SV40 early promoter (Benoist et al., *Nature* 290:304–310 (1981)); and the like. Other useful promoters include liver-specific promoters such as albumin, alpha-fetoprotein, alpha-1-antitrypsin, retinol-binding protein, and others (Fang, X. J. et al., *Hepatology* 10:781–787 (1989)).

Such liver-specific promoters are expected to be particularly useful when a DNA sequence from the polymerase gene, preferably from part of all of the terminal protein domain, is placed in a vector which is capable of transforming hepatocytes. The gene is placed downstream from a suitable promoter which provides for tissue-specific or general expression. The DNA will be transcribed to produce antisense RNA which will hybridize with its target RNA, thereby inhibiting viral replication. One particular vector useful for this task would be one based upon an adenoviral system, such as described by Morsy et al., Abstract SZ 109, "Efficient Adenoviral Gene Transduction in Human and Mouse Hepatocytes In Vitro and in Mouse Liver In Vivo" in *J. of Cellular Biochemistry,* Supplement 17E, Keystone Symposia on Molecular and Cellular Biology, Mar. 29–Apr. 25, 1993, or, alternatively, a retroviral vector such as LNL6, a derivative of the Moloney murine leukemia virus, as described in Rosenberg et al., *N. Eng. J. Med.* 323, No 9:570–578 (1990). Gene transfer into hepatocytes using a defective Herpes Simplex viral vector is described by Lu et al., Abstract, page 66, Abstracts of the Meeting on Gene Therapy, Sept. 22–26, 1992, Cold Spring Harbor Laboratory, Cold Spring Harbor, N.Y. This latter approach is especially valuable for introducing genes into non-dividing hepatocytes, since HSV-1 does not require genomic integration for expression. The DNA and the requisite regulatory elements may also be introduced into hepatocytes using an asialoglycoprotein carrier system as described in Wu et al., *Biotherapy* 3:87–95 (1991).

The desired mutant viral DNA and operably linked promoter may be introduced into a recipient cell as a non-replicating DNA or RNA molecule, which may be either a linear molecule or, more preferably, a closed covalent circular molecule. Since such molecules are incapable of autonomous replication, the expression of the desired antisense molecule may occur through the transient expression of the introduced sequence. Alternatively, where desired, permanent expression may occur through the integration of the introduced sequence into the host chromosome.

The introduced sequence may be incorporated into a plasmid or viral vector capable of autonomous replication in the recipient host; cDNA expression vectors include those described by Okayama, H., *Mol. Cell. Bio.* 3:280 (1983), and others. Viral vectors include retrovirus vectors as taught in WO89/07136 (specifically for expression in hepatocytes) and the references cited therein.

In this manner, the corresponding nucleic acid or a portion of it coding for the specific mutation or for the desired antisense RNA is introduced into the cells of an organism suffering from the viral disease. Expression of the nucleic acid produces a protein or an antisense oligonucleotide which interferes with the viral replication.

It is also recognized that mutant viral genomes can be constructed and used to transfect host cells. The mutant virus is capable of expressing the defective protein. Thus, the cells can effectively fight off viral attack. Where the host is already infected with unaltered virus, infection of the host with mutant virus expressing the defective protein leads to termination of replication of the unaltered virus.

While the use of a defective polymerase protein to inhibit replication is discussed generally, it is recognized that the defective protein is specific for its own virus. That is, a mutation in the hepatitis B virus polymerase gene will produce a defective protein which inhibits or terminates hepatitis B virus replication.

As noted above, the compositions and methods of the invention can be used to terminate viral replication in a wide variety of RNA and DNA viruses.

In one embodiment of the present invention, the methods and compositions are utilized to terminate the replication of hepatitis virus, particularly hepatitis B virus. By site-directed mutagenesis, at least one mutation can be inserted into the viral genome. The mutation can be introduced at a nucleotide position ranging from about nucleotide 2606 to about nucleotide 2823, generally about nucleotide 2700 to about nucleotide 2900, preferably about nucleotide 2798. These regions will also be suitable targets for application of antisense embodiments of the invention. Where the mutation is inserted at position 2798, the mutation will involve an A to C or T to C change, depending upon the strain of HBV used (see Table 1). This particular mutation will result in a corresponding amino acid change from a Thr or Ser to Pro (see Table 1). The resulting mutation completely and irreversibly terminates replication of the hepatitis B virus.

To terminate HBV replication, a DNA species with a mutation is utilized to prime a defective 3.5 kb pregenomic RNA in the reverse transcriptase reaction. Alternatively, the specific piece of viral DNA encoding the defective protein may be supplied to the host cells under the control of a liver specific promoter. Further, a human HBV genome containing the mutation driven by liver specific promoter can be constructed such that one produces infectious interfering viral particles leading to termination of replication of the wild-type hepatitis virus.

In another embodiment, HIV replication can be inhibited. Accordingly, at least one mutation is inserted into the HIV viral genome, in the nucleotide region of the HIV polymerase gene. Generally, the mutation is introduced at a nucleotide position ranging from about nucleotide 1200 to about nucleotide 5500, more generally about nucleotide 1500 to about nucleotide 4700. The resulting mutations will be examined for an effect on viral replication by the methods disclosed herein.

It is believed that the mechanism of termination of viral replication involves the defective production of a protein necessary for encapsidation of pregenomic RNA or of binding protein necessary for initiation of the polymerase reaction. This protein serves as a primer for the reverse transcription of minus strand DNA. However, it is not dependent upon any specific method disclosed herein, other than the insertion of mutations within the polymerase gene. Accordingly, another or a separate mechanism may actually be involved in terminating viral replication.

Another means for disrupting viral replication is to provide the host cell with antisense DNA or RNA. Supplying the antisense DNA or RNA to the virus interferes with replication. Antisense regulation has been described by Rosenberg et al., *Nature* 313:703–706 (1985); Preiss et al., *Nature* 313:27–32 (1985); Melton, *Proc. Acad. Natl. Sci. USA* 82:144–148 (1985); Kim et al., *Cell* 42:129–138 (1985); and Izant et al., *Science* 229:345–352 (1985). In the presence of the antisense DNA or RNA of the invention, the functioning of the naturally existing mRNA or pregenomic RNA is reduced. Thus, antisense regulation may be achieved by introducing into cells a DNA sequence comprising a gene in which the transcribed DNA sequences are at least partially complementary to the polymerase gene or gene region of interest of the virus. The introduced DNA will be under the transcriptional control of a transcriptional initiation region recognized by the host cells, as discussed above. Transcription of the introduced DNA will result in multicopies of an antisense RNA which will be complementary to RNA of the virus and result in reduction of functioning of the naturally existing RNA. Further, ribozymes spanning specific viral gene regions may serve as therapeutic agents (Sarver, N. et al., *Science* 247:1222–1225 (1990)). Alternatively, exogenous DNA or RNA complementary to a target RNA sequence in the polymerase region may be introduced into a host cell. The invention relates to purified and isolated oligonucleotide constructs described herein which are substantially free from host or HBV DNA or RNA.

The invention also relates to a composition of matter consisting essentially of at least one antisense oligonucleotide substantially complementary to an RNA sequence (mRNA or pregenomic RNA) encoded by the polymerase gene of HBV, preferably the terminal protein region of the polymerase gene of HBV, preferably comprising a sequence of at least about 12 nucleotides corresponding to a sequence of nucleotides from about n.t.s. 2598 to about n.t.s. 2998 of HBV subtype adw2, more preferably corresponding to a sequence from about n.t.s. 2698 to about n.t.s. 2898 of HBV subtype adw2, even more preferably a sequence comprising at least about 12 nucleotides corresponding to a sequence of nucleotides from about n.t.s. 2794 to about 2833 of HBV subtype adw2. Preferred is such an antisense oligonucleotide sequence of about 12 to about 40 nucleotides in length, more preferably about 15 to about 30 nucleotides in length, even more preferably about 20 to about 30 nucleotides in length.

As used herein, "substantially complementary" means that an antisense oligonucleotide of the invention is capable of hybridizing with its RNA target under physiological conditions, e.g., as pertains inside an HBV-infected hepatocyte. HBV nucleotide sequence numbering herein is made with reference to the numbering of HBV HBsAg subtype adw2, more particularly subtype adw2 as published in Blum et al., *Hepatology* 14(1):56–63 (1991). By convention, the EcoRI cleavage site present in all known strains of HBV is designated n.t.s. position 0. See Valenzuela P. et al., The nucleotide sequence of the hepatitis B viral genome and the identification of the major viral genes. In: Fields B. N., Jaenisch R., Fox C. F., eds., *Animal Virus Genetics*, pp. 57–70, New York, Academic Press (1980), the teaching of which is hereby incorporated by reference. Corresponding sequences for strains of HBV other than HBV subtype adw2, e.g., the strains listed in Table 1, infra, as well as other strains of HBV that have been and will in the future be isolated and sequenced, can be determined by those of skill in the art by aligning sequences for homology, e.g., by using an available database such as GenBank.

It has been found that 25-, 30-, and 40-mer antisense oligonucleotides substantially complementary to RNA encoded by the HBV polymerase gene, preferably the terminal protein region of that gene, completely block HBV antigen production and replication, whereas the complementary sense oligonucleotides of similar lengths have little or no effect. Moreover, 30-mer antisense oligodeoxynucleotides from conserved regions of the HBV core gene (n.t.s. 1865–1894) and the X gene (n.t.s. 1428–1457), did not reduce viral protein (HBsAg and HBcAg) or inhibit HBV replication. Antisense constructs directed to this same region but of 16 or 20 nucleotides in length exhibited antiviral activity, but to a lesser degree. Accordingly, the invention relates to antisense oligonucleotides of at least about 12 nucleotides in length, and preferably up to about 80 nucleotides in length, more preferably about 15 to 40 nucleotides in length, still more preferably about 15 to 30 nucleotides in length, and most preferably about 20 to 30 nucleotides in length.

HBV oligonucleotides of the invention may be supplied to the target cell, preferably a hepatocyte, as a recombinant DNA molecule operatively linked to a cell-specific promoter which will express the desired antisense RNA oligonucleotide, or the antisense RNA or DNA sequence itself may be supplied directly to a target hepatocyte. The sequences listed below are from replication-defective HBV mutant genome 5-15, which exhibits a critical A to C mutation at nucleotide 2798. However, this missense mutation is not required for the described embodiments of the invention, and the corresponding sequences from other HBV strains, including subtype adw2, can easily be determined, thereby allowing selection of sequences specific for non-human species or for human HBV strains prevalent in particular populations or geographic areas. Alternatively, corresponding consensus or conserved sequences having broader applicability may be determined. The following are some examples of oligonucleotides within the invention (5' to 3'):

HBV OLIGODEOXYNUCLEOTIDES FOR ENDOGENOUS EXPRESSION

GAT-40: GGA ACC CAC ACG TAG CGC ATC ATT TTG CGG GTC ACC ATA T (SEQ ID NO: 1)
GAT-35: A ACC CAC ACG TAG CGC ATC ATT TTG CGG GTC ACC A (SEQ ID NO: 2)
GAT-30: C CAC ACG TAG CGC ATC ATT TTG CGG GTC AC (SEQ ID NO: 3)
GAT-30B: GGA ACC CAC ACG TAG CGC ATC ATT TTG CGG (SEQ ID NO: 4)
GAT-30C: CG TAG CGC ATC ATT TTG CGG GTC ACC A (SEQ ID NO: 5)
GAT-25: AC ACG TAG CGC ATC ATT TTG CGG GT (SEQ ID NO: 6)
GAT-20: CG TAG CGC ATC ATT TTG CGG (SEQ ID NO: 7)
GAT-16: TAG CGC ATC ATT TTG C (SEQ ID NO: 8)
WO 10044: CGC ATC ATT TTG CGG GTC ACC ATA T (SEQ ID NO: 9)
WO 10046: CGC CTC ATT TTG CGG GTC ACC ATA T (SEQ ID NO: 10)

HBV OLIGONUCLEOTIDES SUPPLIED EXOGENOUSLY)

ATC-40: ATA TGG TGA CCC GCA AAA TGA TGC GCT ACG TGT GGG TTC C (SEQ ID NO: 11)
ATC-35: TGG TGA CCC GCA AAA TGA TGC GCT ACG TGT GGG TT (SEQ ID NO: 12)
ATC-30: G TGA CCC GCA AAA TGA TGC GCT ACG TGT GG (SEQ ID NO: 13)
ATC-30B: ATA TGG TGA CCC GCA AAA TGA TGC GCT ACG (SEQ ID NO: 14)
ATC-30C: CC GCA AAA TGA TGC GCT ACG TGT GGG TTC C (SEQ ID NO: 15)
ATC-25: A CCC GCA AAA TGA TGC GCT ACG TGT (SEQ ID NO: 16)
ATC-20B: CC GCA AAA TGA TGC GCT ACG (SEQ ID NO: 17)
ATC-20A: ATA TGG TGA CCC GCA AAA TG (SEQ ID NO: 18)
ATC-20C: A TGC GCT ACG TGT GGG TTC C (SEQ ID NO: 19)
ATC-16B: GCA AAA TGA TGC GCT A (SEQ ID NO: 20)
ATC-16A: ATA TGG TGA CCC GCA A (SEQ ID NO: 21)
ATC-16C: GCT ACG TGT GGG TTC C (SEQ ID NO: 22)
WO 10042: ATA TGG TGA CCC GCA AAA TGA GGC G (SEQ ID NO: 23)

The methods of the present invention can be utilized to prevent viral infection as well as to combat viral infections. The compositions comprising the defective protein vectors containing nucleic acids encoding the defective proteins may be administered to prevent a virus infection or to combat the virus once it has entered the host.

As used herein, "consisting essentially of" has its usual meaning, i.e., that one or more compositions of matter of the invention may be used together, either in admixture or combined in a single molecule, with other materials that do not alter the essential nature of the invention. For example, while the antisense oligonucleotide sequences of the invention are essential to the invention, it is contemplated that they may be used in admixture or in chemical combination with one or more other materials, including other oligonucleotides antisense to HBV RNA, materials that increase the biological stability of the oligonucleotides, or materials that increase their ability to selectively penetrate their hepatocyte target cells and reach and hybridize with their target RNA. Furthermore, the term "oligonucleotide" includes derivatives thereof, such as backbone modifications, e.g., phosphorothioate derivatives, employed to stabilize the oligonucleotides. All such modifications are contemplated equivalents of the antisense oligonucleotides of the invention. The following discussion provides examples of the kinds of modifications that may be employed, but those of skill in the art will readily recognize others. For example, the antisense oligonucleotides may be provided in stabilized form, e.g., with phosphotriester linkages, or by blocking against exonuclease attack with methylphosphonodiester linkages, with 3' deoxythymidine, as a phenylisourea derivative, or by linking other molecules such as aminoacridine or polylysine to the 3' end of the oligonucleotide. See e.g., *Anticancer Research* 10:1169–1182, at 1171–2 (1990), the teaching of which is incorporated herein by reference. For antisense oligonucleotides supplied exogenously, increased selectivity for hepatocytes may be achieved by linking antisense oligonucleotides of the invention to natural ligands such as ASOR (asialoorosomucoid) or to synthetic ligands that will bind to the hepatic asialoglycoprotein (ASGP) receptor. See e.g., *Biochemistry* 29, No. 43 (1990), Spiess, "The Asialoglycoprotein Receptor: A Model for Endocytic Transport Receptors". See also Wu and Wu, *J. Biol. Chem.* 267, No. 18:12436–12439 (1992), reporting inhibition of HBV viral gene expression and replication in HepG2 cells by a 21-mer oligonucleotide complementary to the HBV polyadenylation signal. The oligomer was complexed to a (poly)L-lysine-asialoorosomucoid conjugate that targets the asialoglycoprotein receptor of hepatocytes. In another embodiment, ribozymes may be targeted by linking to an oligonucleotide of the invention. See e.g., Von Weiszaecker F., Blum H. E., Wands J. R., Three ribozymes transcribed from a single DNA template efficiently cleave hepatitis B virus pregenomic RNA, *Biochem. Biophys. Res. Commun.* 189:743–748 (1992). The teaching of the foregoing references is incorporated herein by reference.

In general, a high efficiency cell specific delivery system for in vivo therapeutic use may utilize a number of approaches, including the following: 1) specific delivery through a hepatocyte-specific receptor, such as the asialoglycoprotein receptor, as discussed above; 2) delivery of antisense oligodeoxynucleotides in liposomes with or without specific targeting with monoclonal antibodies directed against specific cell surface receptors; 3) retroviral-mediated transfer of DNA expressing the antisense construct of interest; and 4) direct targeting to cells of anti-sense oligodeoxynucleotides via conjugation to monoclonal antibodies that are specific for cell surface receptors that function in a receptor-mediated endocytotic process; 5) specific delivery to hepatocytes via a replication-defective HBV vector. To modify hepadnaviral infection in vivo, a hepatocyte-specific delivery system whereby all hepatocytes are provided with the antisense construct will probably be required.

The antisense compositions of the invention may be administered as individual therapeutic agents or in combination with other therapeutic agents. They can be administered alone, but are generally administered with a pharmaceutical carrier selected on the basis of the chosen route of administration and standard pharmaceutical practice. The dosage administered will of course vary depending upon known pharmacokinetic/pharmacodynamic characteristics of the particular agent, and its mode and route of administration, as well as the age, weight, and health (including renal and hepatic function) of the recipient; the nature and extent of disease; kind of concurrent therapy; frequency and duration of treatment; and the effect desired. Usually a daily dose of active ingredient can be about 0.1 to 100 mg per kilogram of body weight. Ordinarily 0.5 to 50, and preferably 1 to 10 mg per kg of body weight per day given in divided doses or in sustained release form (including sustained intravenous infusion) will be effective to achieve the desired effects. Dosage forms suitable for internal administration generally contain about 1 milligram to about 500 milligrams of active ingredient per unit. The active ingredient will ordinarily be present in an amount of about 0.5 to 95% by weight of the total pharmaceutical preparation. It is expected that the antisense oligonucleotide compositions of the invention may be administered parenterally (e.g., intravenously, preferably by intravenous infusion). For parenteral administration, the compositions will be formulated as a sterile, non-pyrogenic solution, suspension, or emulsion. The preparations may be supplied as a liquid formulation or lyophilized powder to be diluted with a pharmaceutically acceptable sterile, non-pyrogenic parenteral vehicle of suitable tonicity, e.g., water for injection, normal saline, or a suitable sugar-containing vehicle, e.g., D5W, D5/0.45, D5/0.2, or a vehicle containing mannitol, dextrose, or lactose. Suitable pharmaceutical carriers, as well as pharmaceutical necessities for use in pharmaceutical formulations, are described in *Remington's Pharmaceutical Sciences,* a standard reference text in this field, or the USP/NF. The following examples are offered by way of illustration and not by way of limitation.

EXAMPLE I

Episomal HBV DNA in the liver of an individual serologically immune to HBV infection was previously identified (Blum, H. E. et al., *Liver* 8:307–316 (1988)). The cloning, fine structure analysis, and biologic properties of the viral genome from this individual's liver have been accomplished. The cloned genome showed 48 base changes relative to an infectious HBV of the most closely related serotype adw2 (Valenzuela, P. et al., The nucleotide sequence of the hepatitis B viral genome and the identification of the major viral genes, p. 57–70, In B. N. Fields, R. Jaenisch and C. F. Fox (eds.), Animal virus genetics, Academic Press, Inc. New York (1980)). One of these mutations introduced a stop codon at the end of the pre-core region of the viral genome, prohibiting hepatitis B e antigen (HBeAg) formation. Functional analysis of the cloned DNA by transfection into HuH 7 hepatoma cells indicated competence for synthesis of all major viral transcripts, viral core and envelope proteins but a defect blocking viral DNA replication. The genetic basis of this defect in DNA synthesis was identified to be a single missense mutation in position 2798 leading to a substitution of threonine or serine by proline. This finding suggests a critical role of this polymerase gene region, presumably coding for the terminal protein or a protein required for encapsidation of pregenomic RNA, in the life cycle of the virus, as well as specific therapeutic strategies to terminate viral replication.

To establish the fine structure of the episomal HBV DNA in the patient's liver, the viral genome was amplified from total liver DNA by the polymerase chain reaction (PCR), using three HBV-specific primer pairs (Table 1). The amplified viral DNA fragments were cloned in pGEM-7, yielding the three expected overlapping HBV clones 1-8, 2-13 and 3-1 (Table 1). Using these clones, the HBV DNA molecule was reconstructed and cloned in pGEM-7, yielding the full-length HBV genome 5-15. By direct sequencing of these clones, the complete nucleotide sequence of the HBV genome 5-15 was determined (data submitted to GenBank). The genome has a length of 3221 bases and a genetic organization identical to known HBV DNAs. A comparison to published DNA sequences demonstrated closest homology to HBsAg subtype adw2 (Valenzuela, P. et al., The nucleotide sequence of the hepatitis B viral genome and the identification of the major genes, p. 57–70, In B. N. Fields, R. Jaenisch and C. F. Fox (eds.), Animal virus genetics, Academic Press Inc., New York (1980)). As compared to this subtype, a total of 63 mutations were detected in HBV 5-15, 48 of which resulted in amino acid substitutions. To exclude mutations induced by PCR amplification, mutations leading to amino acid changes were confirmed by cloning and sequencing of independent PCR amplification products. Mutations were identified in all open reading frames with the highest frequency in the pre-C/C region (26 per 1000 bases), a region which otherwise shows the highest degree of homology between different HBV DNAs and other hepadnaviruses (ref. 3 and data available through GenBank). While the mutations resulted in an in-phase stop codon at the end of the pre-C reading frame, resulting in the inability to code for the pre-C/C protein, a precursor to hepatitis B e antigen (HBeAg), the stop codon at the end of the pre-C reading frame was not found in the viral DNA integrated in the patient's hepatocellular carcinoma (data not shown), suggesting that this mutation was not present in the infecting virus but rather occurred during ongoing viral replication in the non-tumorous liver after integration of viral DNA.

Because no direct conclusions with respect to the biology of the virus could be drawn from the structural characteristics described above, the functional competence of the mutant viral genome was analyzed in vitro. Following transfection of HuH 7 hepatoma cells (Nakabayashi, H. et al., *Cancer Res.* 42:3858–3863 (1982)), cell lysates and cell culture media were analyzed for the presence of viral transcripts, proteins and replicative forms of viral DNA. As shown in FIG. 1, hybridization with an HBV-specific probe revealed the presence of two major transcripts of 2.2 and 3.6 kb length, respectively, in both head-to-tail (HTD) adw ('wild-type') and HTD 5-15 ('mutant') transfected cells. No viral transcripts were present in non-transfected cells (data not shown) or in cells transfected with the incomplete HBV clone 1–8 (Table 1). While the level of message was higher in HTD adw2 than in HTD 5-15 transfected cells, the ratio of the 3.6 kb pregenomic to 2.2 kb subgenomic message appears very similar. These findings indicate that the mutant viral genome is competent to synthesize all major HBV transcripts.

HBV-encoded proteins were identified by solid-phase radioimmunoassay, both in cell lysates and culture media. Both HTD adw- and HTD 5-15-transfected HuH 7 cells secrete substantial amounts of HBsAg and HBc/eAg into the media, while no viral antigens are produced by cells transfected with the incomplete clone HBV 1-18 (data not illustrated). As predicted from the stop codon mutation in position 1899, metabolic labeling and immunoprecipitation studies revealed that HTD 5-15 transfected cells are incompetent to synthesize the large pre-C/C protein and its smaller processed products, normally secreted as HBeAg into cell culture media (data not illustrated).

In order to assess the replication competence of the mutant genome 5-15, HBV DNA species were analyzed by Southern blot hybridization of cytoplasmic DNA isolated from HuH 7 cells after transfection. As shown in FIG. 2, replicating HBV DNA species were detected in cells transfected with HTD adw only, while no viral DNA was present in cells transfected with the incomplete clone HBV 1-18 (negative control) or with HTD 5-15. Viral DNA sequences in HTD adw transfected cells represent single-stranded and partially double-stranded replicative intermediates, as well as complete relaxed circular molecules (Blum, H. E. et al., *Virology* 139:87–96 (1984)).

Viral antigens and DNA species in cell lysates and culture media of HTD adw or HTD 5-15 transfected cells were further characterized by CsCl density gradient centrifugation followed by analysis of individual fractions for HBsAg and HBc/eAg and HBV DNA sequences. In HTD adw transfected cells, viral DNA is associated with HBc/eAg (core particles) and in culture media with HBsAg (virions) and HBc/eAg (core particles). As expected, while positive for HBsAg and HBcAg, no viral DNA species were detectable in CsCl fractions of cell lysates or culture media from HTD 5-15 transfected HuH 7 cells. These findings demonstrate that, while HuH 7 cells support viral replication, the mutant HBV genome 5-15 is unable to replicate in this system.

Figure 4:
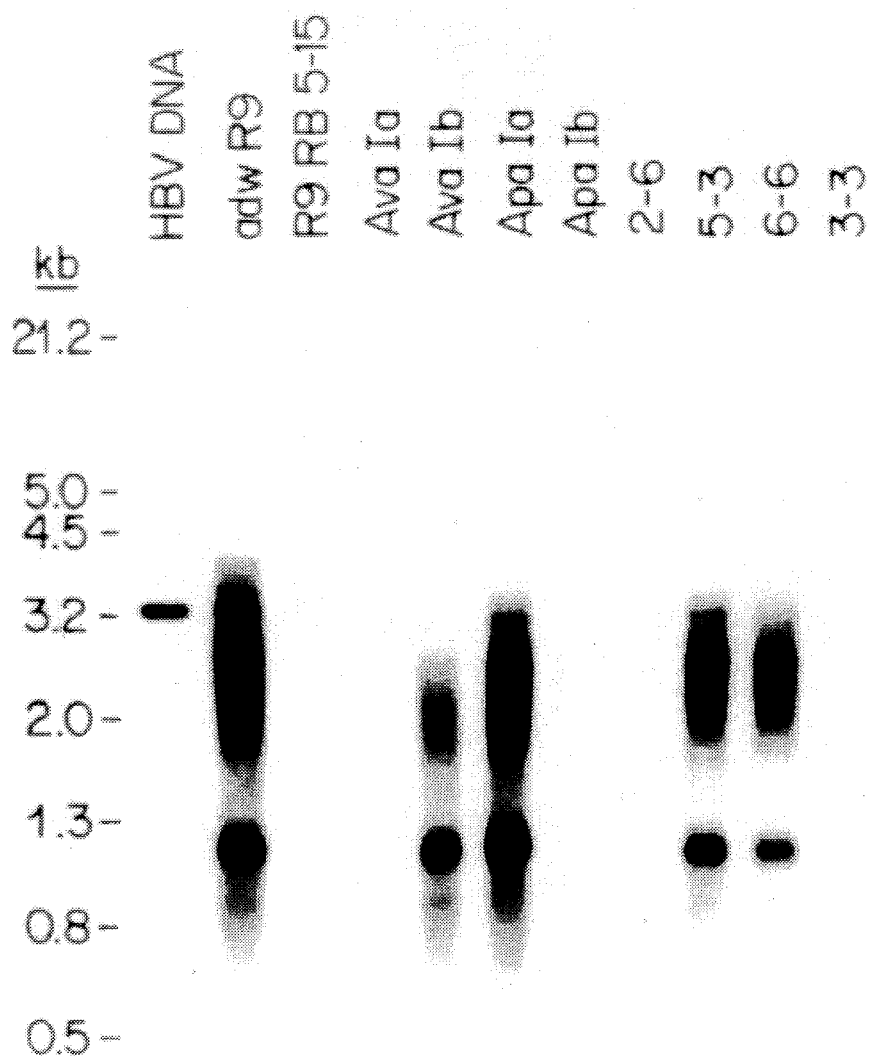
FIG. 4: Nucleotide 2798 is critical to replication competence of HBV DNA. HuH 7 cells were grown and transfected as described in the legend to FIG. 1. Five days after infection, cell culture media were collected and cells were lysed in NP40 (Hirsch et al., Virology 167:136–142 (1988)). Media were centrifuged for 30 minutes at 50,000×g (20° C.). The supernatant was brought to 10 mM MgCl$_2$. After addition of DNase I (1 ug/ml; Worthington) in order to digest input DNA, the solution was layered onto a sucrose cushion and processed as described in the legend to FIG. 2. The equivalent to the cell culture medium from one 100 mm dish (10ml) was applied per lane. Autoradiographic exposure at −80° C. was 12 hours. All cell culture media negative for replicating HBV DNA were also negative in the respective cell lysate preparations (data not shown). The structure and DNA sequence of the constructs, respectively, are given in FIG. 3 and Table 2, respectively.

The molecular basis of the replication-defectiveness was determined by subcloning of specific regions of the mutant viral genome into the truncated replication-competent adw HTD construct adw R9 (FIG. 3). By exchange of specific DNA fragments, cloning and transfection of HuH 7 hepatoma cells, the mutations responsible for the replication-defectiveness could be localized to a region of the mutant viral genome mapping between position 2606 (Apa 1) and 2823 (Bst EII; FIGS. 3 and 4). Within this region the mutant viral genome has only two missense mutations (nucleotide position 2798 and 2820) relative to adw2 (Valenzuela, P. et al., The nucleotide sequence of the hepatitis B viral genome and the identification of the major viral genes, p. 57–70, In B. N. Fields, R. Jaenisch and C. F. Fox (eds.), Animal virus genetics, Academic Press Inc., New York (1980)). By site-directed mutagenesis of either adw R9 or R9 RB 5-15 (FIG. 3) and primers carrying either the 2798 or the 2820 mutation, four clones were generated by PRC amplification (Table 3): adw R9 with an A to C mutation in position 2798 (clone 2-6), adw R9 with a G to C mutation in position 2820 (clone 5-3), Ava Ia with a C to A mutation in position 2798 (clone 6-6), and Ava Ia with a C to G mutation in position 2820 (clone 3-3). After transfection of HuH 7 hepatoma cells with these clones, it could be demonstrated that the A to C mutation of clone adw R9 in position 2798 renders viral DNA replication-defective while the C to A mutation of clone Avala in the same position reestablishes replication competence (FIG. 4). By contrast, the mutation in position 2820 did not affect the replication competence or defectiveness of the parent constructs (clone 3-3 and clone 6-6). These findings unequivocally demonstrate that the A to C mutation in position 2798 of the viral genome, leading to a Thr to Pro substitution, is the molecular basis for the replication defect of the mutant viral genome isolated from the patient's liver.

Experimental studies (Bosch, V. et al., *Virology* 166:474–485 (1988); Bartenschlager, R. et al., *EMBO J.* 7:4185–4192 (1988); Schlicht, H. -J. et al., *Cell* 56:85–92 (1989)) and comparative structural and hydropathy analyses of hepadnavirus polymerases (Khudyakov, Y. E. et al., *FEBS Letters* 243:115–118 (1989)) suggest that the 5' region of the viral polymerase gene encodes the "terminal protein" (TP). This protein binds to the 5' end of minus strand DNA and presumably serves as a primer for reverse transcription, which is a central feature of the replication strategy of the hepadnaviruses (Seeger, C. et al., *Science* 232:477–484 (1986); Will, H. et al., *J. Virol.* 61:904–911 (1987)). Mutational analyses of the duck hepatitis B virus polymerase gene indeed demonstrated that an in-frame insertion into the 5' region of this gene eliminates the production of an active polymerase (Schlicht, H. -J. et al., *Cell* 56:85–92 (1989)). These data strongly suggest that the TP region of the polymerase gene is important for viral replication. Further, the functionally intact polymerase gene appears to be required for the packaging of pregenomic RNA. Consistent with this interpretation, the mutation identified in nucleotide position 2798 in our mutant or produced by mutagenesis of 'wild type' virus terminates viral replication. The significance of this mutation is further emphasized by the fact that the amino acid in position 164 of the polymerase gene product is highly conserved in all HBV strains (11/14 Thr, 3/14 Ser), as shown by a comparison with the published HBV DNA sequences (Okamoto et al., *J. Gen. Virol.* 69:2575–2583 (1988)) and those available through the GenBank. The mechanism of this termination of viral replication is possibly mediated through conformational change of the TP or a protein involved in the encapsidation of genomic RNA due to a Thr or Ser to a Pro substitution.

Cotransfection of HuH 7 hepatoma cells with wild type HBV and mutant HBV DNA demonstrated that the mutant was capable of terminating replication of the wild type HBV. See Table 4. When HBV and unrelated DNA were used to transfect HuH 7 cells, replication of the hepatitis virus was not hindered, as evidenced by hybridization of total cellular DNA with HBV viral DNA. No viral DNA was detected in cells cotransfected with mutant virus DNA, indicating that the mutant was able to terminate replication of the wild type hepatitis virus.

The capability of a mutant virus to terminate replication of nonmutant viruses has important implications. In those individuals or hosts suffering from a viral infection, the mutant virus can terminate the replication of the virus in infected cells and prevent the virus from spreading to other cells.

TABLE 1

Comparison of conservation of AA position 164 in the polymerase gene of various HBV strains

| HBV Strain | AA-164 | NT. 2798 |
|---|---|---|
| 1. vadw2 | Thr | A̲CC |
| 2. adr | Thr | ACT̲ |
| 3. ayr | Thr | ACT̲ |
| 4. adra | Thr | ACT̲ |
| 5. adrm | Thr | ACT̲ |
| 6. adrcg | Thr | ACT̲ |
| 7. adw1 | Ser | T̲CA |
| 8. adw2 | Ser | TCC̲ |
| 9. adw3 | Thr | A̲CA |
| 10. adw | Thr | A̲CC |
| 11. vcg chimp | Thr | A̲CC |
| 12. adyw | Ser | T̲CA |
| 13. ayw | Thr | A̲CA |
| 14. hpv | Thr | ACT̲ |
| * Mutant (no replication) | Pro | C̲C̲C̲ |

*A single mutation e.g. A to C at position 2798 converts Thr to Pro or a T to C mutation at position 2798 converts Ser to Pro.

Table 2: Position and Sequences of HBV Specific Oligonucleotide Primers used for PCR Amplification and Cloning of HBV DNA from the Patient's Liver.

A 73-year old white male with a history of viral hepatitis presented with metastasizing hepatocellular carcinoma (HCC). HBV serology was negative for HBsAg and anti-HBc IgM and positive for anti-HBc IgG, anti-HBe and anti-HBs, as determined by radioimmunoassays (Abbott, North Chicago, Ill.). No HBV DNA could be detected in serum by spot-blot hybridization. Liver and HCC tissues obtained at autopsy were stored at −80° C. until use. Liver DNA was amplified using Taq polymerase and primers carrying restriction enzyme sites at the 5' and 3' ends (Table 2). The polymerase chain reaction (PRC) was performed according to Saiki et al. (Saiki, R. et al., Science 239:487–491 (1988)). Briefly, target sequences were amplified in a 50 ul reaction volume containing 50 ng DNA, 2.5 units of Taq polymerase (Perkin-Elmer Cetus), 200 uM each dNTP, 1 uM each primer, 50 ml/1 KCl, 10 mM Tris-HCl, pH 8.3, 1.5 mMMgCl$_2$, and 0.01% (wt/vol) gelatin. The reaction was performed for 40 cycles in a programmable DNA thermal cycler (Perkin-Elmer Cetus). Samples were heated to 94° C. for 1.5 min (denaturation of DNA), cooled to 50° C. for 1.5 min (hybridization to primer), and incubated for 3 min at 72° C. (polymerase reaction). After PCR, 5 units of Klenow polymerase were added to complete strand synthesis and to ensure cleavage by the appropriate restriction endonucleases. The PCR mixture was fractionated on a 1.25% agarose gel in the presence of ethidium bromide. The band containing the target sequence was removed and DNA was isolated by glass beads (Geneclean, Bio 101 Inc., La Jolla, Calif.). The purified fragments were ligated into pGEM-7Zf(+) (Promega) and cloned in DH5aF' cells (BRL). Cloned DNA was prepared by standard plasmid preparation. The three clones 1-18, 2-13 and 3-1 (Table 2) were used to reconstruct the full-size viral genome (clone 5-15). For transfection experiments, head-to-tail dimers of HBV DNA HBsAg subtype adw2 ('wild-type') and of HBV DNA 5-15 were constructed in pGEM-7Zf(+) and cloned as described above. DNA sequence analysis was performed as described (Mierendorf, R. C. et al. Meth. Enzymol. 152:556–562 (1987)) using the Gem Seq RT system (Promega) or the T7 polymerase system (Pharmacia).

TABLE 2

| Primer Pair 1-8: | |
|---|---|
| 1: 3119–3142 | 5'-CCGAGCTCCACCAATCGGCAGTCAGGAAG-3' (SEQ ID NO: 24) |
| 2: 1449–1428 | 5'-CGATCGATTCAGCGCCGACGGACGTA-3' (SEQ ID NO: 25) |
| Target Sequence: | 5'-Sac I 1552 bp Cla 1-3' (clone 1-8) |
| Primer Pair 2-13: | |
| 3: 1865–1889 | 5'-CAGAATTCAAGCCTCCAAGCTGTGCCTTGG-3' (SEQ ID NO: 26) |
| 4: 0248–0224 | 5'-AGTCTAGACTCTGCGGTATTGTGAGGATTCTTG-3' (SEQ ID NO: 27) |
| Target Sequence: | 5'-Eco RI 1604 bp Xba 1-3' CLONE 2-13) |
| Primer Pair 3-1: | |
| 5: 1281–1307 | 5'-CGGAGCTCCTAGCCGCTTGTTTTGCTCGCAGC-3' (SEQ ID NO: 28) |
| 6: 2430–2410 | 5'-GAAAGCTTCTGCGACGCGGCGATTGAGA-3' (SEQ ID NO: 29) |
| Target Sequence: | 5'-Sac I 1150 bp Hind III-3' (clone 3-1) |

Table 3: DNA Sequence of In Vitro Mutagenesized HBV DNA Clones and Their Parent Constructs Clones adw R9 and R9 5-15 (see FIG. 3) were amplified by PCR (see Table 1) using a generic primer spanning the region 2312 to 2333 (CC-22) and a primer spanning the region 2833 to 2794, carrying either a T to G mutation in position 2798 (ATC-40) or a C to G mutation in position 2820 (ACC-40). The amplified fragments were purified by agarose gel electrophoresis and Geneclean (Bio 101 Inc., La Jolla, Calif.). After digestion with Apa I and Bst EII, the fragments were cloned into adw R9 (see FIG. 3), yielding the four clones: 2-6, 3-3, 5-3 and 6-6, carrying the expected single point mutation.

TABLE 3

| Clone | DNA Sequence | | | | | Replication |
|---|---|---|---|---|---|---|
| | | 2798 | 2820 | | | |
| 5adw R9 | 2791 - GAGGGAAACC | ACACGTAGCG | CATCATTTTG | CGGGT | - 2825 (SEQ ID NO: 30) | + |
| 2-6 | 2791 - | C | | | - 2825 | − |
| 5-3 | 2791 - | | | C | - 2825 | + |
| Ava Ia | 2791 - GAGGGAACCC | ACACGTAGCG | CATCATTTTC | CGGGT | - 2825 (SEQ ID NO: 31) | − |
| 6-6 | 2791 - | A | | | - 2825 | + |
| 103-3 | 2791 - | | | G | - 2825 | − |

Table 4: Cotransfection with mutant HBV

HuH 7 cells were cotransfected with: 1) wild type HBV and unrelated DNA; and 2) wild type HBV and mutant HBV DNA. The unrelated DNA utilized for cotransfection was a neomycin resistance-carrying vector.

After cotransfection, replication of the virus was determined by extraction of total cellular DNA followed by hybridization with labelled HBV DNA. Following extraction, total cellular DNA was digested with DNase and RNase followed by centrifugation in a sucrose mixture. Viral DNA was taken from the sucrose gradient and subjected to gel electrophoresis. Following electrophoresis, the DNA was transferred to nitrocellulose and treated with labelled viral DNA. The resulting autoradiographs showed the presence of viral DNA in cells cotransfected with wild type HBV and unrelated DNA. No viral DNA was detected in the cells transfected with wild type HBV and mutant HBV DNA.

TABLE 4

| Cotransfection | Replication |
|---|---|
| 1. Wild type HBV and unrelated DNA | + |
| 2. Wild type HBV and mutant HBV DNA | − |

+ indicates replication of HBV as evidenced by hybridization with viral DNAs
− no replication detected

EXAMPLE II

Inhibition of Hepatitis B Virus by Antisense Oligodeoxynucleotide 40met

Figure 5A:
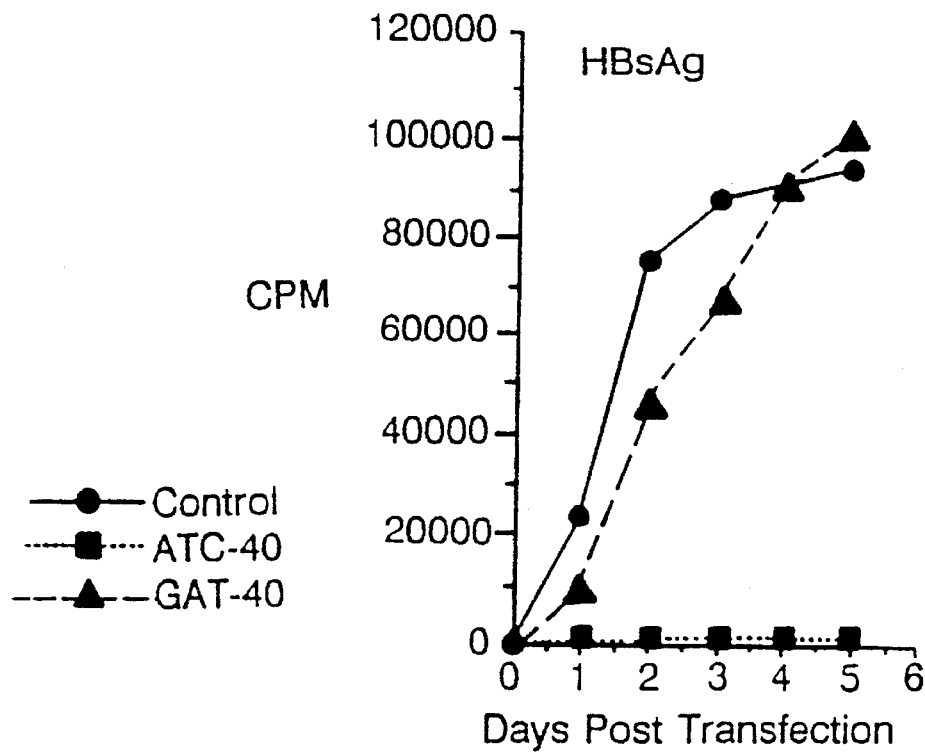
FIGS. 5A and 5B: Inhibition of viral antigen synthesis by HBV-specific antisense oligodeoxynucleotide. Detection of HBsAg (5A) and HBeAg (5B) in cell culture medium after transfection of human hepatoma cells (HuH 7) with HBV-DNA alone (────●──── control), HBV-DNA plus an antisense oligodeoxynucleotide (·······■······· ATC-40), or HBV-DNA plus a sense oligodeoxynucleotide (──────▲────── GAT-40). Analyses were completed with commercially available radioimmunoassays (Centocor, Malvern, Pa. and Abbott, Chicago, Ill., USA).
Figure 5B:
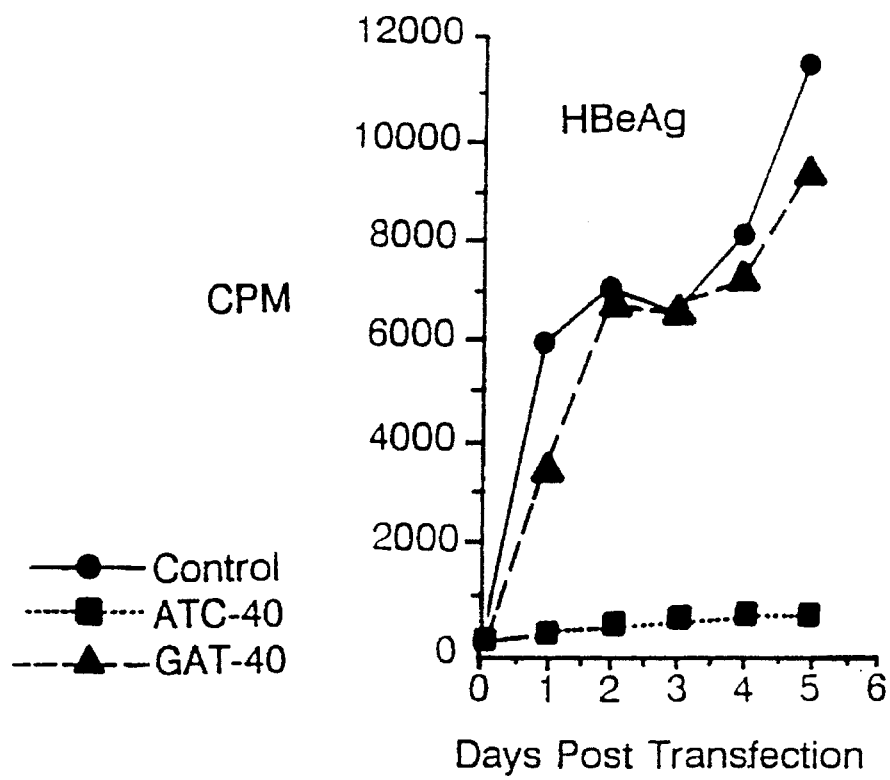
Figure 6:
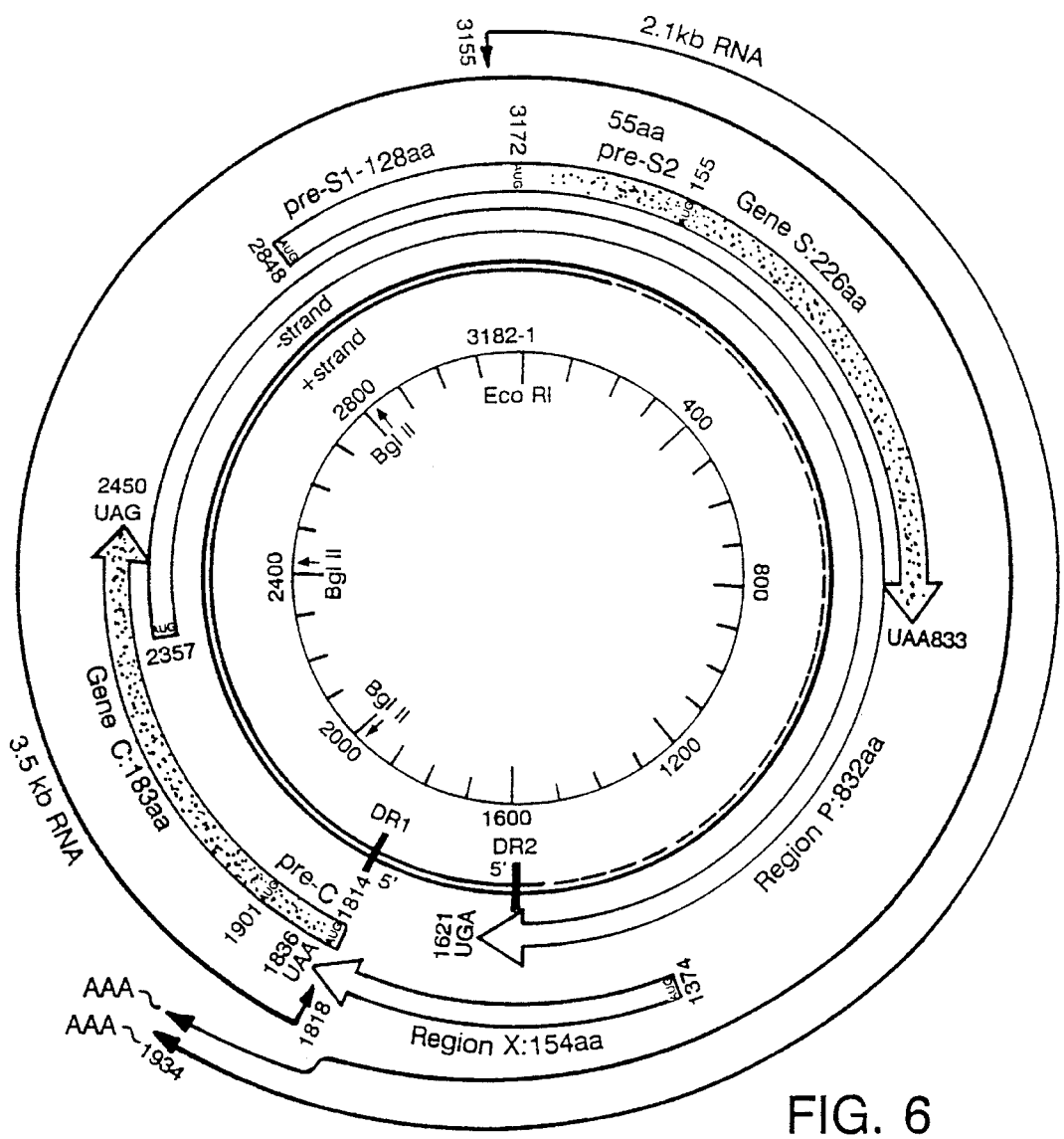
FIG. 6: Map of the HBV genome showing the coding organization of the four major open reading frames (the pre-S and S gene which code for the HBsAg; the C gene, which codes for HBcAg and HBeAg; the P gene which codes for the HBV DNA polymerase; and the X gene, which codes for the transactivating X protein, HBX), as well as the 3.5 kb pregenomic RNA and the 2.1 kb subgenomic RNA species.

The effect of antisense oligodeoxynucleotides on HBV gene expression and replication was analyzed. Transfection of human hepatoma cells with HBV-DNA (Blum et al., *J. Virol* 682:1836–42 (1991)) (control) resulted in the synthesis and secretion of hepatitis B surface antigen (HBsAg) and hepatitis B e antigen (HBeAg). Cotransfection of HBV-DNA with an oligodeoxynucleotide of antisense polarity (ATC-40 see below) completely blocked HBsAg and HBeAg synthesis, as well as HBV replication (FIG. 5). The same oligodeoxynucleotide of sense polarity (GAT-40) had no effect on viral antigen production or replication. Co-transfection of HBV DNA with the ACC-40 antisense oligodeoxynucleotide also completely blocked HBV replication, indicating that the T to G mutation at n.t.s. 2798 is a marker for a gene product which plays an important role in HBV replication. This region is within the domain of the polymerase gene encoding the HBV terminal protein (TP).

Oligodeoxynucleotide Preparation 1. adw 2833–2794 (2798 5-15 T to G mutation)
ATC-40 5' ATATGGTGAC CCGCAAAATG ATGCGC-TACG TGTGGGTTCC 3' (SEQ ID NO: 11)

2. adw 2833–2794 (2820 5-15 C to G mutation)
ACC-40 5' ATATGGTGAC CCGGAAAATG ATGCGC-TACG TGTGGTTTCC 3' (SEQ ID NO: 32)

TABLE 5

| | $A_{260}$ | $A_{280}$ | $A_{260/280}$ | ng/μL | μg total |
|---|---|---|---|---|---|
| ATC-40 | 0.132 | 0.084 | 1.57 | 2.64 | 1.32 |
| ACC-40 | 0.259 | 0.149 | 1.67 | 5.18 | 2.59 |

EXAMPLE III

Inhibition of Hepatitis B Virus by Additional Antisense Oligodeoxynucleotides

Synthesis and Purification of Oligodeoxynucleotides. Unmodified sense and antisense oligodeoxynucleotides derived from three different HBV genes (FIGS. 7, 13A, and 14A) were prepared by standard phosphoramidite chemistry made on a Milligen/Biosearch 8750 DNA synthesizer and then purified after NH$_4$OH detachment (55° C., 6 hours) and NAP 25 column (Pharmacia) desalting with 0.1M NaHCO$_3$ by reverse phase HPLC (trityl on, TEAA 0.1M, pH 7.25/ acetonitrile gradient). The oligodeoxynucleotides were lyophilized, deblocked with 1M acetic acid for 1 hour, neutralized with TEA, passed through a NAP 10 column and then lyophilized to dryness.

Transfection of HUH-7 cells and analysis of HBV-specific proteins. HUH-7 cells (Nakabayashi H., et al., Growth of human hepatoma cell lines with differentiated functions in chemically defined medium. *Cancer Res.* 42:3858–3863(1982)) were grown to near confluency in Eagle's Minimal Essential Medium supplemented with 10% fetal calf serum. Cells were transfected as described by Chen and Okayama (High efficiency transformation of mammalian cells by plasmid DNA. *Mol. Cell. Biol.* 7:2745–2752 (1987)), routinely using 2.5 ug of a head-to-tail (HTD) dimer of HBV DNA subtype adw constructed in pGEM-7Zf(+) (Promega Corp.) (Blum et al., *J. Virol.* 65:1836–1842 (1991)) plus different amounts of oligodeoxynucleotides per 60 mm plate. HBsAg and HBc/eAg were determined by commercially available radioimmunoassays and enzyme immunoassays (Centocor, Malvern, Pa. and Abbott Laboratories, N. Chicago, Ill.).

DNA and RNA Analysis. For the preparation of core-associated HBV DNA, transfected cells were lysed in 20 mM Tris (pH 7.5), 100 mM NaCl, 0.5% Nonidet P-40, 1 mM EDTA. The lysate was centrifuged at 50,000×g for 1 hour at 20° C. After the addition of MgSO$_4$ to a final concentration of 10 mM, the supernatant was incubated with 23 U of DNase I (Boehringer Mannheim) per ml for 6 hr at 37° C. The solution was layered on a 30% sucrose cushion and centrifuged at 178,000×g for 5 hr at 4° C. The pellet (core particles) was digested with 10 mM Tris (pH 7.6), 10 mM EDTA, 1% sodium dodecyl sulfate (SDS), 500 ug of proteinase K per ml for 16 hr at 37° C.. Nucleic acids were phenol extracted as described previously (Sambrook et al., Molecular Cloning: A Laboratory Manual, 2nd Ed., Cold Spring Harbor, N.Y.). RNA was prepared by the guanidine isothiocyanate method (Davis et al., Basic Methods in Molecular Biology, Elsevier Pub. Co., NY (1986)).

DNA was fractionated by 1.25% agarose gel electrophoresis in Tris-acetate EDTA buffer (Sambrook et al. supra). RNA was analyzed by formaldehyde, 1.0% agarose gel electrophoresis (Davis et al., supra). Nucleic acids were transferred to Nytran membranes (Schleicher & Schuell, Inc., Keene N.H.). The membranes were prehybridized for 6 hr at 42° C. in 50% (v/v) formamide, 5×SSC (1×SSC is 0.15M NaCl plus 0.015M sodium citrate), 2.5×Denhardt's solution (1×Denhardt's solution is 0.02% polyvinyl-pyrrolidone, 0.02% Ficoll, 0.02% bovine serum albumin), 0.1% SDS, 1 mM EDTA, 5 mM NaH$_2$PO$_4$, 200 ug of denatured fragmented salmon sperm DNA per ml. Hybridization with recombinant full-length HBV DNA labeled to high specific activity (2–4×10$^8$ cpm/ug) was performed in the above buffer for 16 hr at 42° C. After hybridization, membranes were washed twice in 1×SSC, 0.1% SDS for 15 min at room temperature and twice in 0.1×SSC, 0.1% SDS for 1 hr at 60° C. Membranes were exposed to Kodak XAR X-ray film at −80° C.

Figure 7:
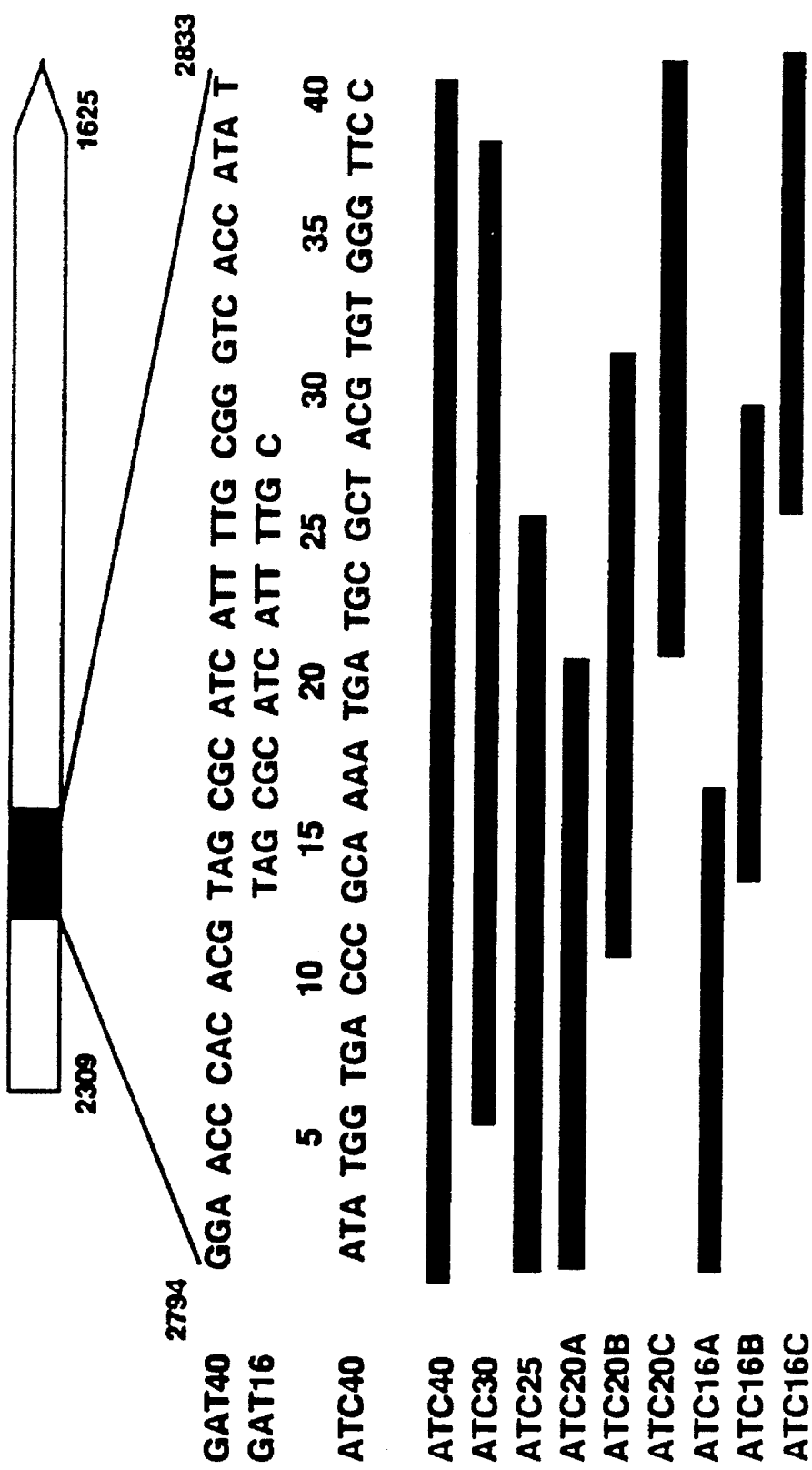
FIG. 7: Diagram of the sequence and origin of various HBV-specific oligonucleotides derived from the polymerase gene. A series of antisense (ATC) and sense (GAT) constructs varying from 16 to 40 nucleotides in length are shown.

Effect of oligonucleotide derived from the HBV polymerase region. A series of overlapping oligonucleotides of various lengths were synthesized as shown in FIG. 7. We have shown this region of the HBV polymerase gene to contain a natural point mutation at nucleotide position 2798 that rendered the variant virus incapable of replication. As shown in Example II, a 40-mer antisense oligodeoxynucleotide spanning nucleotide position 2798 exhibited the ability to block viral replication. In order to establish whether this general region of the polymerase mRNA could serve as a target sequence for antisense oligodeoxynucleotides, we co-transfected sense and antisense constructs with adw HTD HBV DNA and subsequently measured HBV antigen levels, RNA transcripts and replicative intermediates.

Figure 8A:
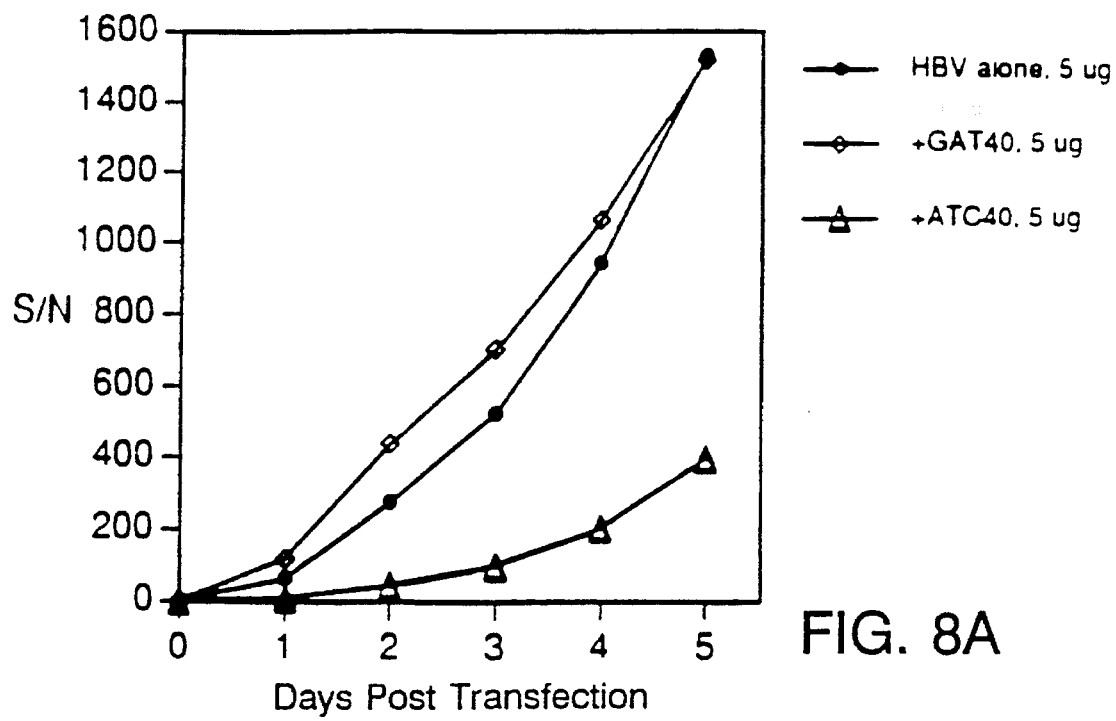
FIG. 8A: Effect of ATC 40 and GAT 40 on HBsAg expression at a ratio of 1:1 (wt/wt) of HBV DNA to oligonucleotide. There was substantial but not complete inhibition of HBsAg synthesis by the antisense construct.
Figure 8B:
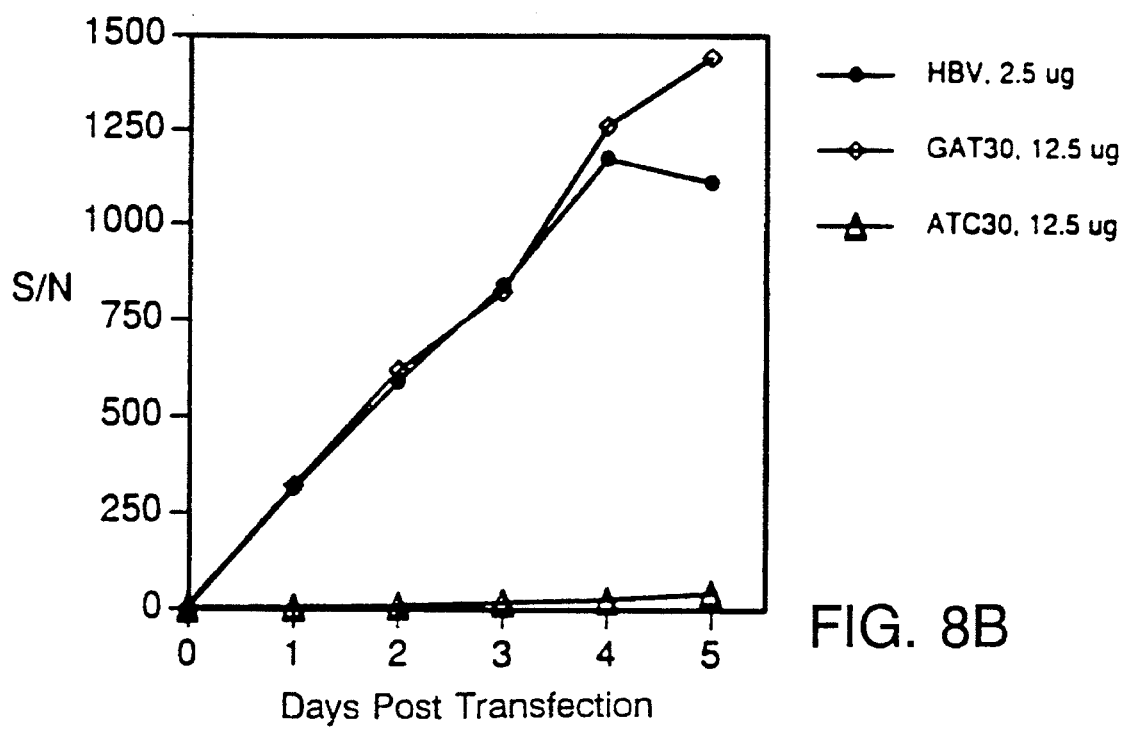
FIG. 8B: Effect of GAT 30 and ATC 30 on HBsAg synthesis at a HBV DNA target to oligonucleotide ratio of 1:5. There was complete inhibition of HBsAg synthesis with antisense ATC 30.
Figure 8C:
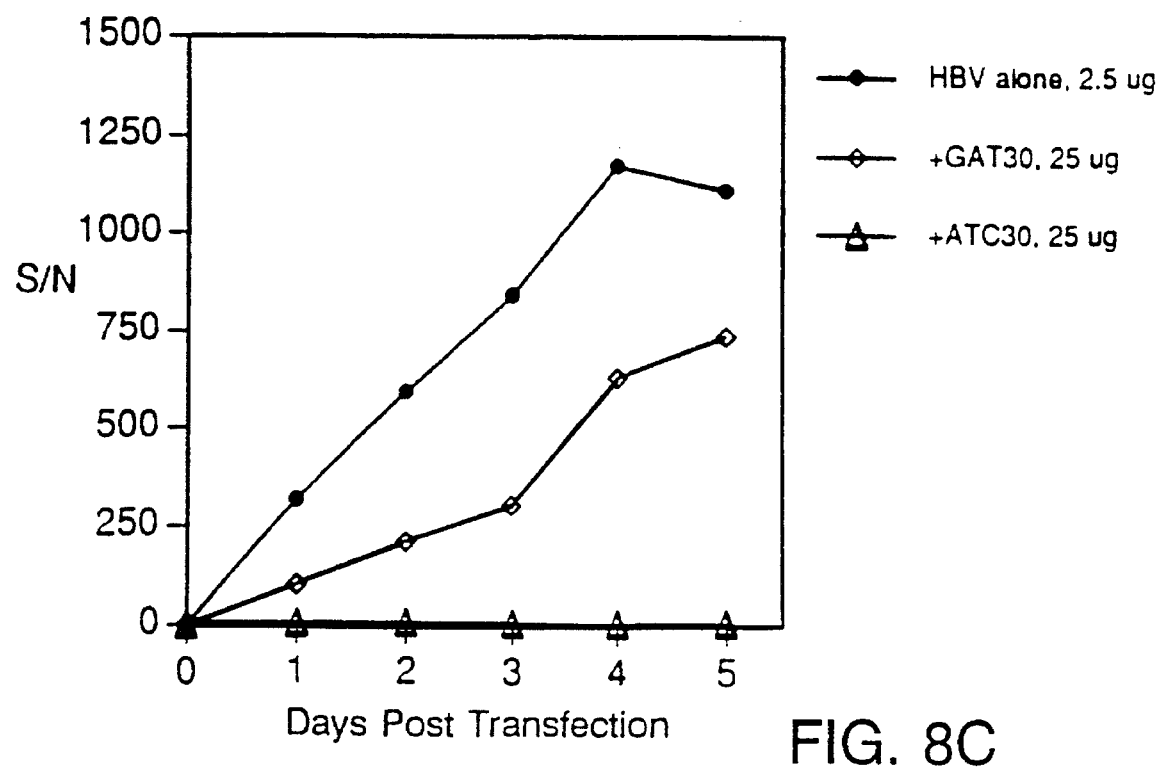
FIG. 8C: Effect of ATC 30 and GAT 30 at a 1:10 ratio demonstrating partial inhibition of HBsAg synthesis by the sense construct as well.

Experiments were first performed to determine the optimal ratio of HBV DNA-containing plasmid to oligodeoxynucleotide to achieve a maximal antisense effect. FIG. 8A demonstrates the effect on HBsAg synthesis in the culture medium using adw HTD HBV DNA plus the sense 40-mer oligodeoxynucleotide (GAT 40) or antisense (ATC 40) constructs at a 1:1 ratio (wt/wt). No inhibition of HBsAg levels were observed in cells co-transfected with GAT 40 compared to cells transfected with adw HBV DNA alone. However, there was substantial but not complete inhibition of HBsAg synthesis and secretion using antisense ATC 40 oligonucleotide as measured over a 5 day period. When the ratio of HBV DNA target sequence to oligodeoxynucleotide was changed to 1:5, we found complete inhibition of HBsAg synthesis and secretion by the antisense ATC 40 compared to the sense GAT 40 transfected under identical experimental conditions. Similar findings were obtained with a 1:5 ratio of a 30-mer antisense oligodeoxynucleotide as shown in FIG. 8B, resulting in complete inhibition of HBsAg synthesis and secretion by antisense ATC 30, but not be the sense GAT 30 construct. FIG. 8C demonstrates the effect of the GAT 30 and ATC 30 at a ratio of 1:10. Under these conditions, there was also a partial inhibition of HBsAg synthesis and secretion by the sense GAT 30-mer oligodeoxynucleotide. These experiments revealed that the optimal ratio of target HBV DNA to antisense oligodeoxynucleotide to achieve a reproducible, polarity-specific, and complete inhibition of HBsAg synthesis was 1:5.

Figure 9A:
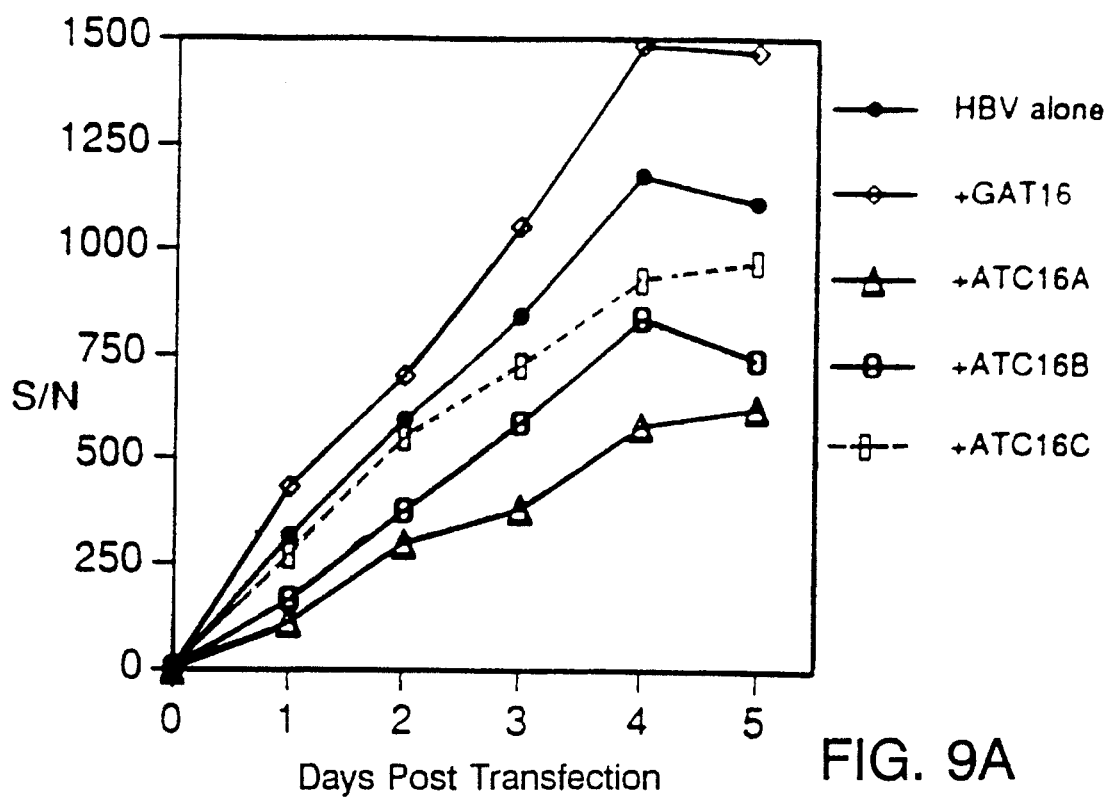
FIG. 9A: Effect of oligonucleotide length on HBsAg synthesis. These antisense constructs span the 40 nucleotide HBV polymerase gene region depicted in FIG. 1. There was only partial reduction of HBsAg levels in the culture medium by antisense constructs of 16 nucleotides in length.
Figure 9B:
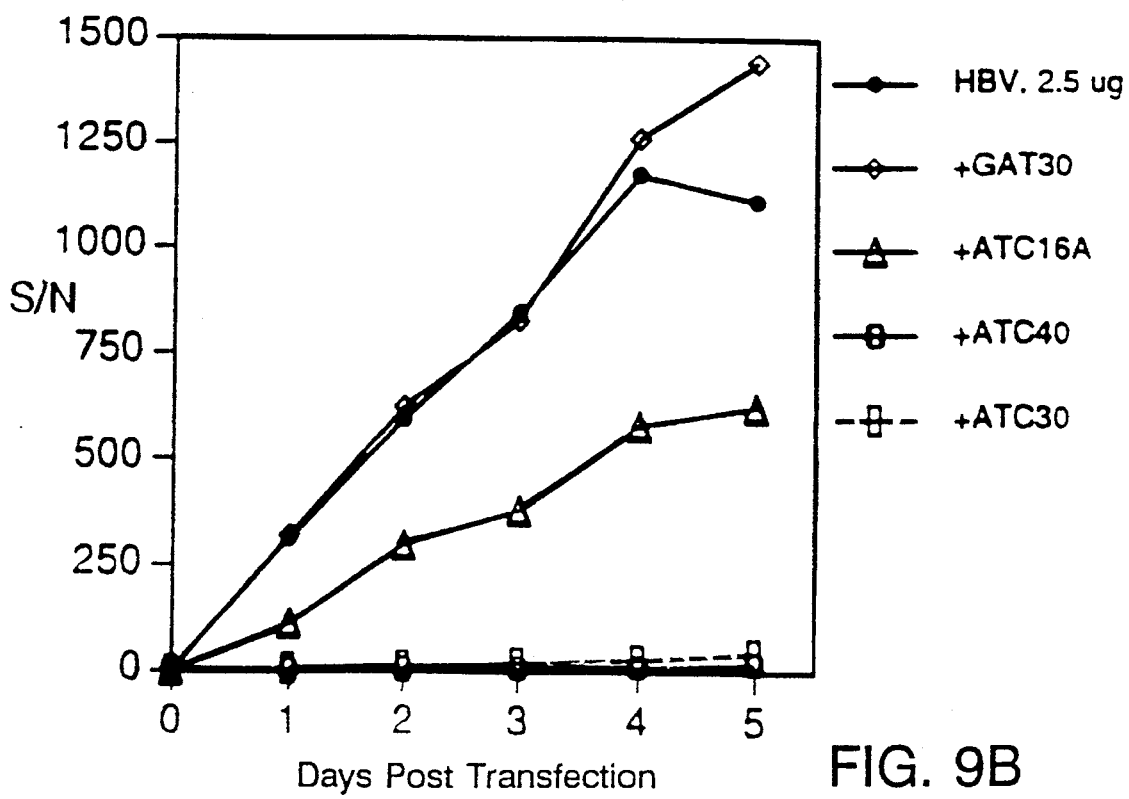
FIG. 9B: Inhibition of HBsAg synthesis by the antisense ATC 30 and ATC 40 constructs compared to the antisense ATC 16A, the sense GAT 30, and adw2 HTD HBV DNA alone.

Experiments were then performed to assess oligodeoxynucleotide length on HBsAg synthesis and secretion. FIG. 9A demonstrates the effect of three 16-mer antisense oligodeoxynucleotides that span the entire 40 nucleotide region depicted in FIG. 7 (ATC 16A, ATC 16B and ATC 16C, respectively). There was essentially no effect on HBsAg levels in the culture medium by the antisense oligodeoxynucleotide ATC 16C. Some inhibition was observed with antisense construct ATC 16B and a modest effect was apparent with ATC 16A. FIG. 9B summarizes the action of antisense constructs of various lengths on HBsAg synthesis and secretion. Complete inhibition was observed with ATC 40 and ATC 30 as well as ATC 25 (data not shown). Approximately 50% inhibition was seen with ATC 16A and ATC 20A. Minimal if any inhibition was observed with ATC 20B and ATC 20C (data not shown) These studies demonstrate that both oligodeoxynucleotide length and sequence specificity are important to produce an antiviral effect under these experimental conditions.

Figure 10A:
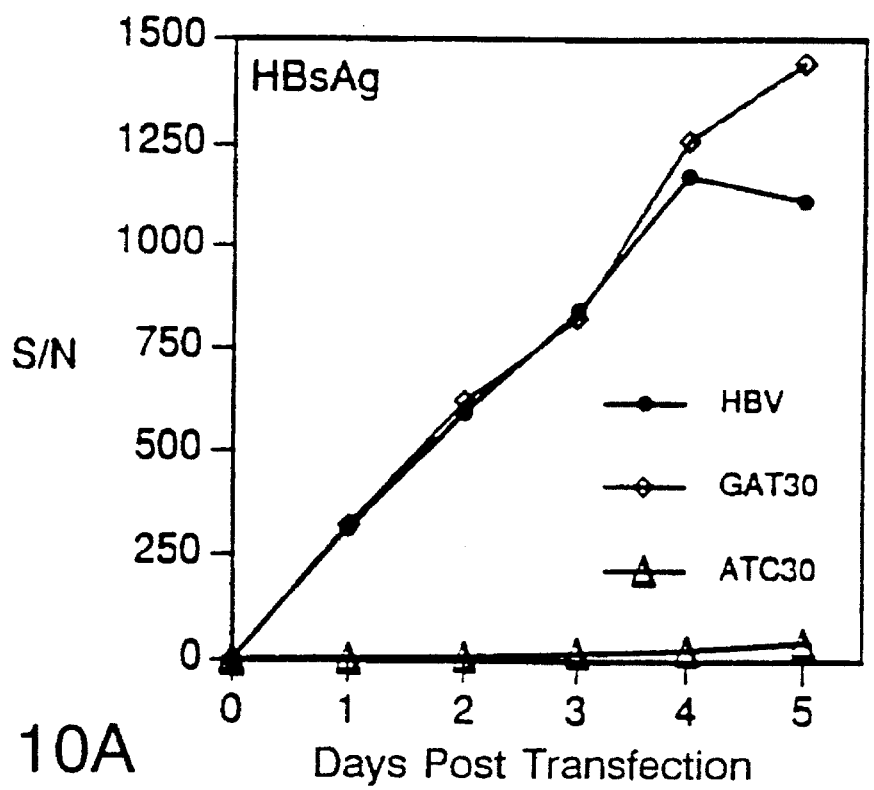
FIGS. 10A and 10B: Effect of sense and antisense 30-mer constructs derived from the polymerase gene region of HBsAg (A) and HBeAg (B) synthesis following co-transfection with adw2 HTD HBV DNA. There was complete inhibition of HBsAg and HBeAg synthesis and secretion into the culture medium of HUH-7 cells by ATC 30.
Figure 10B:
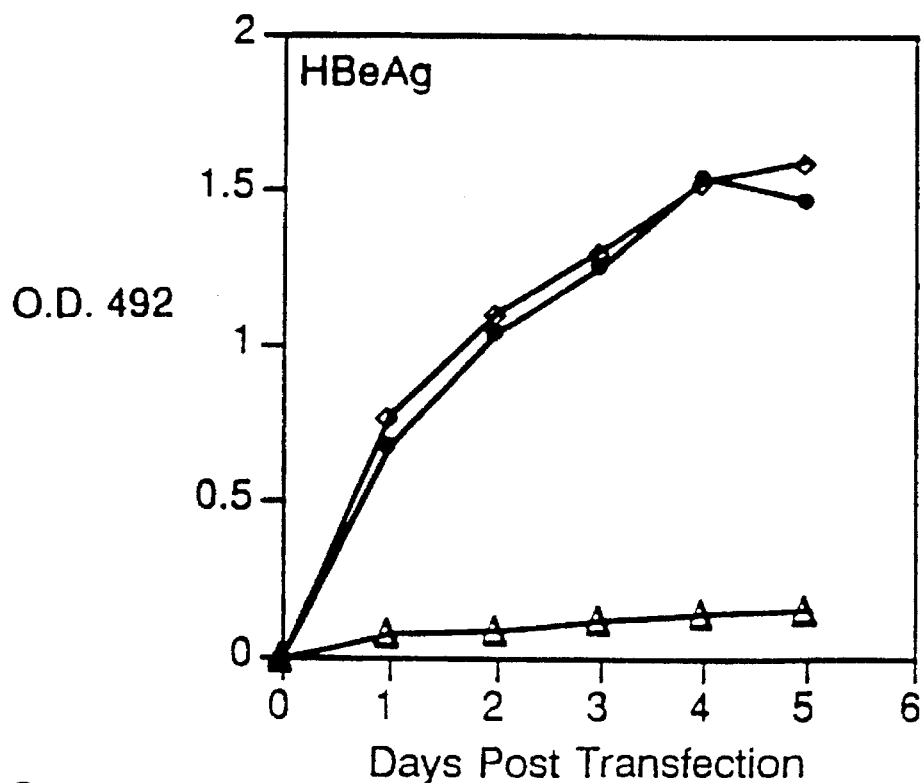
Figure 11:
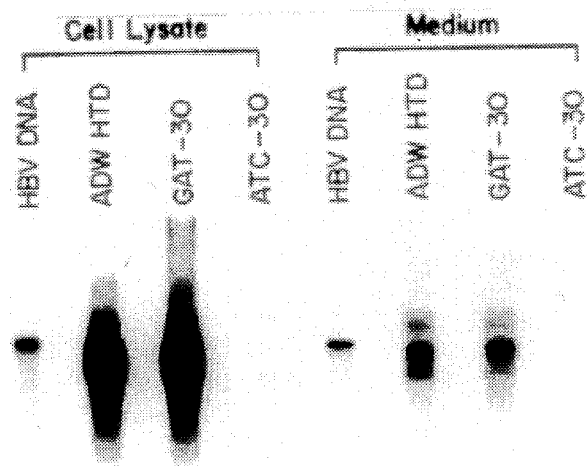
FIG. 11: Effect of oligodeoxynucleotides on HBV DNA replication. Left hand side represents Southern blot analysis of HBV DNA derived from cell lysates 5 days 5 following co-transfection. Co-transfection with the antisense oligodeoxynucleotide ATC 30 but not the sense construct resulted in complete inhibition of HBV DNA replication. Analysis of HBV virions secreted into the medium revealed a similar effect of the various oligonucleotide constructs as shown on the right hand side of the figure.

FIGS. 10A and 10B show the antiviral effects of antisense ATC 30 compared to sense GAT 30 on HBeAg and HBsAg expression over 5 days of culture. These experiments also demonstrated complete suppression of surface and nucleocapsid viral protein synthesis by ATC 30, but not by GAT 30 (FIG. 10B). Southern blot analyses were performed at day 5 following transfection of adw HTD HBV DNA alone or in combination with GAT 30 or ATC 30 oligonucleotides, as shown in FIG. 11. Previous experiments had demonstrated that HBV DNA replication was maximal in HUH-7 cells 5 days after transfection. HBV replication was completely blocked by the antisense ATC 30, but not by sense GAT 30. Culture medium from transfected cells was also examined for the presence of HBV virions by Southern blot analysis as described in Blum et al., supra. There was no detectable encapsidated HBV DNA in the culture medium of cells co-transfected with the antisense oligonucleotide ATC 30.

Figure 12:
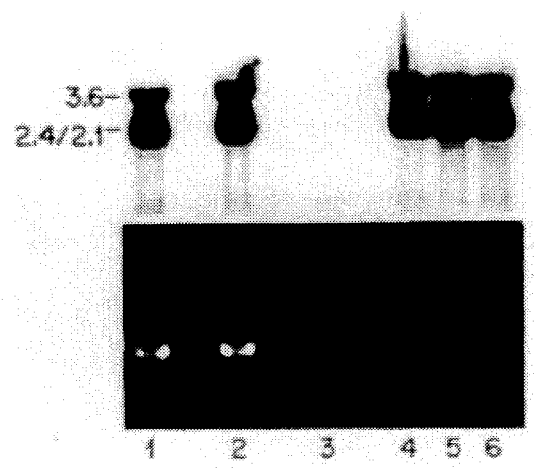
FIG. 12: Northern blot analysis of HBV mRNA two days after co-transfection of ATC 30 and ATC 30 constructs with HBV DNA. Lane 1, adw2 HTD HBV DNA alone; Lane 2, GAT 30; Lane 3, ATC 30; Lane 4, 30-mer core region antisense construct (See FIG. 14A); Lanes 5 and 6, X region sense and antisense 30-mer constructs. The bottom panel indicates ethidium bromide staining of total cellular RNA applied to each lane. The 3.6 kb HBV pregenomic mRNA and the subgenomic 2.4/2.1 kb species were not observed in HUH-7 cells treated with the polymerase gene antisense oligodeoxynucleotide ATC 30 (Lane 3).

To explore the mechanism(s) of this antisense effect, Northern blots were performed to detect and characterize HBV gene transcripts. Previous investigations had demonstrated that expression of HBV mRNA was maximal 2 days after transfection. As shown in FIG. 12, Northern blot analysis demonstrated the absence of both the 3.6 kb pregenomic mRNA as well as the subgenomic 2.4/2.1 kb species in HUH-7 cells co-transfected with the antisense ATC 30 oligodeoxynucleotide.

Effect of oligodeoxynucleotides derived from the HBV pre-core region on viral gene expression and replication. To determine whether the antiviral effect of HBV antisense oligodeoxynucleotides was gene-specific, additional constructs were prepared from a highly conserved sequence in the HBV pre-core gene. In the experiment illustrated in FIGS. 13B and 13C, sense and antisense 30-mer oligodeoxynucleotides from the pre-core gene were co-transfected with adw HBV HTD DNA, and viral protein synthesis (HBsAg and HBeAg) was measured over a 5 day period; HBV RNA was assessed at day 2 and HBV DNA at day 5 post-transfection. Core gene-derived sense and antisense constructs co-transfected at a HBV DNA target-to-oligodeoxynucleotide ratio of 1:5 resulted in no inhibition of HBsAg secretion by HUH-7 cells, as shown in FIG. 13B. Similarly, there was no decrease in HBcAg levels in the culture medium (FIG. 13C). Finally, there was no effect on HBV gene transcription or viral DNA replication studied at days 2 and 5 after transfection, by either the sense or antisense construct (FIG. 12 and data not shown).

Effect of oligodeoxynucleotides derived from the HBV X region on viral gene expression and replication. Additional sense and antisense oligodeoxynucleotides were synthesized encoding a highly conserved region of the HBV X gene. FIG. 14A depicts the sequences of 30-mer sense and antisense oligodeoxynucleotides prepared from the 5' end of the X open reading frame. The results of co-transfection of the X gene-derived sense and antisense constructs with adw HTD HBV DNA and subsequent measurement of HBsAg and HBeAg levels are presented in FIGS. 14B and 14C. Co-transfection at a ratio of 1:5 resulted in no inhibition of the synthesis of these two viral proteins. Similarly, there was no effect of these two oligodeoxynucleotides on HBV replication when measured 5 days after transfection (data not shown).

EXAMPLE IV

Transfection of HuH 7 cells. HuH 7 hepatoma cells (*Cancer Research* 42:3858–3863 (1982)) were seeded into 6 well plates (35 mm/well) and grown to 70–90% confluency in Dulbecco's Minimal Essential Medium supplemented with 10% fetal bovine serum. Cells were transfected according to a modification of the procedure described by Chen and Okayama (*Mol. Cell. Biol.* 7:2745–2752 (1987). [The modification in this procedure was to incubate the cells in an atmosphere of 5% $CO_2$ throughout the experiment as opposed to incubating the cells in a lower $CO_2$ atmosphere during the actual transfection step.]

Cells were transfected in duplicate with 800 ng of plasmid containing HTD HBV subtype adw2 genome, plus varying amounts of oligonucleotide or carrier DNA per 35 mm well. Cell supernatants were harvested post-transfection on a daily basis for up to 6 days, and cells refed daily with 2 mls of medium/well. The supernatants were stored at 420 C. until assayed for the presence of HBsAg using the Auszyme Monoclonal Diagnostic Kit, a commercially available enzyme immunoassay from Abbott Laboratories, North Chicago, Ill. Assay lots ##75001M1012 and 74319M100 were used in the experiments detailed herein.

Oligonucleotides. The following oligodeoxynucleotides were synthesized in a Milligen Biosearch 8750 DNA synthesizer, using asialoethyl-phosphoramidite syntheses (*Tetrahedron Lett.* 22:1859–1862 (1981)):

WO 10042, 25-mer antisense:
5' ATATGGT GA CCC GC AAAA TGA TGCG 3' (SEQ ID NO: 23)

WO 10044, 25-mer sense:
5' CGCATCA TTTTGC GGGTCA CCA TAT 3' (SEQ ID NO: 9)

CP 10046, 25-mer scramble of antisense sequence:
5' GAG CTCCTGATA ACC GGA GTAAGGA 3' (SEQ ID NO: 33)

WOC20003, 18-mer antisense:
5" TGTT CCC AA GAATAT GGT 3' (SEQ ID NO: 34)

WOC20004, 18-mer scramble of antisense:
5' GCAT CATT ATAA TT CGGG 3' (SEQ ID NO: 35)

WOC20002, 23-mer antisense:
5' TGTT CCC AAGAATAT GGT GACCC 3' (SEQ ID NO: 36)

WOC20001, 23-mer scramble of antisense sequence:
5' TAC GCAGCAGA CCTTT AGT CGT A 3' (SEQ ID NO: 37)

Results. The effect of the oligonucleotides described above on the replication of HBV was tested by transfection of HuH 7 cells with 800 ng of plasmid DNA containing HBV genome and varying amounts of oligonucleotide or 800 ng of plasmid alone.

With the 25-mer antisense oligonucleotide WO 10042 (5' ATATGGT GA CCC GC AAAA TGA TGCG 3'; SEQ ID NO: 23), there was no detectable accumulation of HBsAg in cell supernatants. The 25-mer sense, the 25-mer scramble of antisense, the 23-mer scramble and the 23-mer antisense oligonucleotide slightly decreased the amount of HBsAg present in supernatants compared to control supernatants from cells transfected with plasmid DNA alone. The 18-mer antisense and 18-mer scrambled oligonucleotide had no effect on the accumulation of HBsAg in cell supernatants.

The 25-mer antisense oligonucleotide sequence is contained within the ATC-40 antisense oligonucleotide which corresponds to HBV adw2 2794-2833 (described in Example II supra) and which also completely inhibits HBsAg accumulation. (Numbering herein of HBV subtype adw2 is according to Blum et al., *Hepatology Vol.* 14(No.1):56–63 (1991); see FIG. 1 at 58.) The 25-mer antisense oligonucleotide also inhibits the replication of duck hepatitis B virus in duck hepatocytes. Sequence complementarity studies indicate that only 12 out of the 25 nucleotides in this oligo are present as the complementary nucleotide in the duck hepatitis B virus genome. See Table 6 infra. The complementary nucleotides are present as a sequence of 11 nucleotides-ATTTTGCGGGT (SEQ ID NO: 38), corresponding to nucleotides 2815–2825 of the genome of HBV subtype adw2, and a 12th complementary nucleotide, T at nucleotide 2813. The conservation of this particular sequence of 11 or 12 nucleotides between the two viruses suggests that this sequence is important for viral viability. Although the conserved sequence is entirely contained within both the 25-mer antisense, WO 10042, and ATC-40, only four of the conserved nucleotides are represented in the 23-mer antisense oligonucleotide. Moreover, the inactive 18-mer included none of the conserved sequence. This may explain the decreased activity of the 23-mer and the inability of the 18-mer antisense oligonucleotide to turn off HBsAg expression.

Antisense oligoribonucleotides or oligodeoxyribonucleotides which contain nucleotides corresponding to all or substantially all of the conserved sequence are preferred. When employed as an antisense oligodeoxynucleotide delivered exogenously to a host cell, such an oligodeoxynucleotide would comprise all or substantially all of the sequence ACCCGCAAAAT (SEQ ID NO: 40) or ACCCG-CAAAAT.A (SEQ ID NO: 41) (where . represents a non-complementary nucleotide, preferably the nucleotide present in the target strain of HBV, e.g., G in HBV subtype adw2). When employed as a DNA sequence introduced for transcription by the host cell, the DNA would comprise all or substantially all of the sequence ATTTTGCGGGT (SEQ ID NO: 38) or T.ATTTTGCGGGT (SEQ ID NO: 39) (where . represents a noncomplementary nucleotide, preferably the nucleotide present in the target strain of HBV, e.g., C in HBV subtype adw2).

TABLE 6

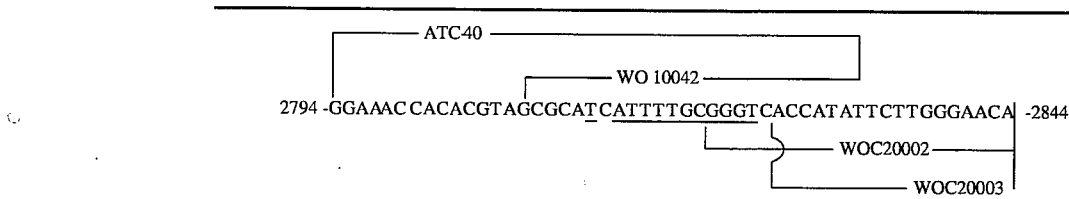

HBV subtype adw2 viral genome corresponding to the antisense oligomers:
ATC-40, which corresponds to nucleotides 2794–2833 (SEQ ID NO: 11);
WO 10042, 25-mer which corresponds to nucleotides 2809–2833 (SEQ ID NO: 23);
WOC20002, 23-mer which corresponds to nucleotides 2822–2844 (SEQ ID NO: 36);
WOC20003, 18-mer which corresponds to nucleotides 2827–2844 (SEQ ID NO: 34).
Sequences conserved in duck hepatitis B virus are underlined. The complementary nucleotides are present as a sequence of 11 nucleotides, ATTTTGCGGGT (SEQ ID NO: 38), corresponding to nucleotides 2815–2825 of the genome of HBV subtype adw2, and a 12th complementary necleotide, T at 2813.
Numbering of HBV subtype adw2 according to Blum et al., Hepatology Vol. 14(No. 1), 56–63, see FIG. 1 at 58 (1991).

DISCUSSION

Example I describes a naturally-occurring replication defective HBV mutant found in the uninvolved liver of an individual with HCC. Fine molecular analysis of this variant HBV revealed an A to C mutation at position 2798 in the 5' region of the polymerase gene, resulting in a threonine to proline change in the terminal protein region of the viral polymerase. This amino acid change rendered the HBV non-replicative, due to an inability to package pregenomic RNA into the core particles. Thus, molecular characterization of this naturally occurring HBV mutant suggested a potential region of the viral mRNA that may be susceptible to attack by the action of antisense oligodeoxynucleotides. In this context, we explored the effects of oligodeoxynucleotide length, as well as concentration, on adw HTD HBV DNA gene expression and replication using a transient co-transfection system with HUH-7 cells. It was striking that 40, 30 and 25-mer antisense oligonucleotides in close proximity to or spanning the naturally occurring point mutation in the 5' region of the polymerase gene completely inhibited HBV gene expression and replication. Shorter constructs of 20 and 16 oligodeoxynucleotides were substantially less effective. Sense constructs had no inhibitory effect as long as the optimal HBV DNA target to oligonucleotide ratio of 1:5 (wt/wt) was maintained. Indeed, using this transient transfection system, the concentration of oligonucleotides was shown to be very important in assessing their anti-viral effects. For example, increasing concentrations of sense oligonucleotides (FIGS. 8A-8C) resulted in inhibition of HBsAg synthesis and secretion into the culture medium, particularly at a DNA target to oligodeoxynucleotide ratio of 1:10. Increasing the concentration of the sense oligodeoxynucleotide even further to a ratio of 1:20 resulted in complete inhibition of HBsAg synthesis. We interpret these findings to indicate that either the transfection efficiency diminishes substantially with increasing DNA concentration as previously observed by others (Chen and Okayama, supra) or the oligodeoxynucleotides at high concentrations are toxic to the cells. However, there appears to be little, if any, effect on HUH-7 cell viability as measured by Trypan Blue exclusion at the concentrations of oligodeoxynucleotides employed (data not shown). More importantly, we have identified a region of the polymerase mRNA, i.e., the terminal protein domain, that is particularly susceptible to the anti-viral effects of antisense oligodeoxynucleotides, since oligodeoxynucleotides derived from other highly conserved regions of the viral genome, namely, the core and X gene, had no such effect. Surprisingly, the region of mRNA highly susceptible to antisense attack is not limited to sequences encompassing mRNA corresponding to the site mutation at n.t.s. 2798 of the polymerase gene, but extends to a broader region of the terminal protein domain of the HBV polymerase gene. Furthermore, the magnitude of the antiviral effects exhibited by antisense oligonucleotides derived from the terminal protein domain of the HBV polymerase gene was noteworthy since there was 100% inhibition of viral gene expression and replication. A recent study of antisense oligodeoxynucleotides targeted via the asialogycoprotein receptor in HepG2 cells (2.2.1.5.) stably transfected with HBV (Wu and Wu, Specific inhibition of hepatitis B virus gene expression in vitro by targeted antisense oligodeoxynucleotides. *J. Biol. Chem.* 267:12436–12439 (1992)) revealed a maximal 80% reduction in HBsAg synthesis and HBV replication. In that study, a 21-mer oligodeoxynucleotide directed against the HBV polyadenylation signal was used as the antisense DNA. Other investigators have achieved antiviral effects varying between 50-80% specific inhibition of human immunodeficiency virus infection (HIV) in vitro using 21-mer antisense oligodeoxy-nucleotides spanning various regions of the viral genome (Agrawal et al., *Proc. Natl. Acad. Sci. USA* 86:7790–7794 (1989); Goodchild et al., *Proc. Natl. Acad. Sci. USA* 85:5507–5511 (1988)). In both of these studies, phosphorothioate derivatives were employed to render the oligodeoxynucleotides less susceptible to nuclease digestion. In the present investigation, we have not altered the native phosphodiester bonds of the oligodeoxynucleotide sequence to prolong the half-life and stability of the antisense constructs. It is likely, therefore, that the observed antiviral effects on intracellular HBV replication may be obtained at considerably lower concentrations of oligodeoxynucleotides if their stability can be improved without affecting binding affinity to target mRNA sequences.

Although the invention disclosed herein is not predicated upon any particular mechanism or theory of operation, the molecular mechanism(s) by which the polymerase gene region antisense oligodeoxynucleotides effect HBV replication may be due in part to hybrid-induced translational arrest or hybrid-induced HBV mRNA degradation by RNAase H. This latter mechanism appears most likely in our system in view of the absence of mRNA species after cotransfection of adw HTD HBV DNA and ATC-30 (see FIG. 12). Likewise, the lack of inhibition by antisense oligodeoxynucleotides derived from highly conserved core and X-region sequences needs further explanation. One possibility is that the secondary structure of HBV mRNA in these latter two regions does not allow sufficient base pairing of the antisense oligodeoxynucleotides to the target mRNA sequences to produce an antiviral effect. In general, antisense oligodeoxynucleotides in proximity to or spanning the AUG codon have been found most effective with respect to inhibition of gene expression. In addition, previous studies with retroviruses have shown that antisense constructs prepared against target sequences in the LTR and at the splice junction sites are highly effective in preventing viral replication, presumably through a RNAase H activation mechanism. Surprisingly, in the present invention, antisense oligodeoxynucleotides considerably downstream from the AUG codon in the polymerase gene completely inhibited the generation of pre-genomic 3.6 kb RNA as well as the subgenomic 2.4/2.1 kb HBV RNA species in HuH 7 cells. The precise molecular mechanisms that result in degradation or translational arrest of the 2.4/2.1 kb HBV mRNA will require additional study, since the antisense oligonucleotides from the polymerase gene region should not form hybrids with these two HBV mRNA species.

All publications and patent applications mentioned in the specification are indicative of the level of skill of those skilled in the art to which this invention pertains. All publications and patent applications are incorporated herein by reference to the same extent as if each individual publication or patent application were specifically and individually stated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for inhibiting replication of hepatitis B virus in a cultured cell, comprising introducing into said cell an antiviral antisense oligonucleotide the sequence of which consists of 12 to 40 contiguous nucleotides of (a) ATC-40: ATA TGG TGA CCC GCA AAA TGA TGC GCT ACG TGT GGG TTC C (SEQ ID NO: 11), or (b) the RNA equivalent of ATC-40, whereby hepatitis B virus replication is inhibited.

2. A method of claim 1, wherein said cell is a hepatocyte.

3. A method of claim 1, wherein the oligonucleotide is an oligodeoxynucleotide.

4. A method of claim 1, wherein the antisense oligonucleotide is 15 to 30 nucleotides in length.

5. A method of claim 1, wherein the antisense oligonucleotide is 15 to 40 nucleotides in length.

6. A method of claim 5, wherein the antisense oligonucleotide is 20 to 40 nucleotides in length.

7. A method of claim 1, wherein said introducing step is accomplished by introducing into the cell a DNA molecule which is transcribed within the cell to produce the antisense oligonucleotide as an oligoribonucleotide.

8. A method of claim 1, wherein the antisense oligonucleotide comprises a sequence identical to at least eight nucleotides of the DNA sequence ACCCGCAAAAT (SEQ ID NO: 38), or the equivalent RNA sequence.

9. A method of claim 7, wherein the antisense oligonucleotide comprises the RNA equivalent of a DNA sequence identical to at least eight nucleotides of ACCCGCAAAAT (SEQ ID NO: 38).

10. A composition of matter consisting essentially of at least one antisense oligonucleotide having antiviral activity against HBV, the sequence of which oligonucleotide consists of 12 to 40 contiguous nucleotides of (a) ATC-40: ATA TGG TGA CCC GCA AAA TGA TGC GCT ACG TGT GGG TTC C (SEQ ID NO: 11), or (b) the RNA equivalent of ATC-40.

11. A composition of matter of claim 10, wherein the antisense oligonucleotide is 15 to 40 nucleotides in length.

12. A composition of matter of claim 11, wherein the antisense oligonucleotide is 20 to 40 nucleotides in length.

13. A composition of matter of claim 10, wherein the antisense oligonucleotide is an oligodeoxynucleotide.

14. A composition of matter of claim 10, wherein the antisense oligonucleotide comprises at least nine nucleotides of the DNA sequence ACCCGCAAAAT (SEQ ID NO: 38), or the equivalent RNA sequence.

15. A composition of matter of claim 10, wherein said antisense oligonucleotide is 15 to 30 nucleotides in length.

16. A composition of matter of claim 10, wherein the antisense oligonucleotide has a DNA sequence, or equivalent RNA sequence, selected from the group consisting of (5' to 3'):

ATC-40: ATA TGG TGA CCC GCA AAA TGA TGC GCT ACG TGT GGG TTC C (SEQ ID NO: 11),

ATC-35: TGG TGA CCC GCA AAA TGA TGC GCT ACG TGT GGG TT (SEQ ID NO: 12),

ATC-30: G TGA CCC GCA AAA TGA TGC GCT ACG TGT GG (SEQ ID NO: 13),

ATC-30B: ATA TGG TGA CCC GCA AAA TGA TGC GCT ACG (SEQ ID NO: 14),

ATC-30C: CC GCA AAA TGA TGC GCT ACG TGT GGG TTC C (SEQ ID NO: 15),

ATC-25: A CCC GCA AAA TGA TGC GCT ACG TGT (SEQ ID NO: 16),

ATC-20B: CC GCA AAA TGA TGC GCT ACG (SEQ ID NO: 17),

ATC-20A: ATA TGG TGA CCC GCA AAA TG (SEQ ID NO: 18),

ATC-16B: GCA AAA TGA TGC GCT A (SEQ ID NO: 20),

ATC-16A: ATA TGG TGA CCC GCA A (SEQ ID NO: 21), and

WO 10042: ATA TGG TGA CCC GCA AAA TGA GGC G (SEQ ID NO: 23).

17. A nucleic acid which (a) can be replicated in a hepatocyte, and (b) is transcribed in a hepatocyte to produce an antiviral antisense oligoribonucleotide the sequence of consists of 12 to 40 contiguous nucleotides of the RNA equivalent of ATC-40: ATA TGG TGA CCC GCA AAA TGA TGC GCT ACG TGT GGG TTC C (SEQ ID NO: 11).

18. The composition of matter of claim 10, wherein the antisense oligonucleotide comprises a sequence identical to the DNA sequence ACCCGCAAAAT (SEQ ID NO: 38), or the equivalent RNA sequence.

19. The composition of matter of claim 18, wherein the antisense oligonucleotide comprises the RNA equivalent of ACCCGCAAAAT (SEQ ID NO: 38).

20. A method of claim 1, wherein the antisense oligonucleotide has a DNA sequence, or equivalent RNA sequence, selected from the group consisting of (5' to 3'):
ATC-40: ATA TGG TGA CCC GCA AAA TGA TGC GCT ACG TGT GGG TTC C (SEQ ID NO: 11),
ATC-35: TGG TGA CCC GCA AAA TGA TGC GCT ACG TGT GGG TT (SEQ ID NO: 12),
ATC-30: G TGA CCC GCA AAA TGA TGC GCT ACG TGT GG (SEQ ID NO: 13),
ATC-30B: ATA TGG TGA CCC GCA AAA TGA TGC GCT ACG (SEQ ID NO: 14),
ATC-30C: CC GCA AAA TGA TGC GCT ACG TGT GGG TTC C (SEQ ID NO: 15),
ATC-25: A CCC GCA AAA TGA TGC GCT ACG TGT (SEQ ID NO: 16),
ATC-20B: CC GCA AAA TGA TGC GCT ACG (SEQ ID NO: 17),
ATC-20A: ATA TGG TGA CCC GCA AAA TG (SEQ ID NO: 18),
ATC-16B: GCA AAA TGA TGC GCT A (SEQ ID NO: 20),
ATC-16A: ATA TGG TGA CCC GCA A (SEQ ID NO: 21), and
WO 10042: ATA TUG TGA CCC GCA AAA TGA GGC G (SEQ ID NO: 23).

21. A nucleic acid of claim 17, wherein the antisense oligoribonucleotide has a nucleotide sequence selected from the group consisting of the RNA equivalents of (5' to 3'):
ATC-40: ATA TGG TGA CCC GCA AAA TGA TGC GCT ACG TGT GGG TTC C (SEQ ID NO: 11),
ATC-35: TGG TGA CCC GCA AAA TGA TGC GCT ACG TGT GGG TT (SEQ ID NO: 12),
ATC-30: G TGA CCC GCA AAA TGA TGC GCT ACG TGT GG (SEQ ID NO: 13),
ATC-30B: ATA TGG TGA CCC GCA AAA TGA TGC GCT ACG (SEQ ID NO: 14),
ATC-30C: CC GCA AAA TGA TGC GCT ACG TGT GGG TTC C (SEQ ID NO: 15),
ATC-25: A CCC GCA AAA TGA TGC GCT ACG TGT (SEQ ID NO: 16),
ATC-20B: CC GCA AAA TGA TGC GCT ACG (SEQ ID NO: 17),
ATC-20A: ATA TGG TGA CCC GCA AAA TG (SEQ ID NO: 18),
ATC-16B: GCA AAA TGA TGC GCT A (SEQ ID NO: 20),
ATC-16A: ATA TGG TGA CCC GCA A (SEQ ID NO: 21), and
WO 10042: ATA TGG TGA CCC GCA AAA TGA GGC G (SEQ ID NO: 23).

22. The nucleic acid of claim 17, wherein the antisense oligoribonucleotide comprises the RNA equivalent of at least eight nucleotides of ACCCGCAAAAT (SEQ ID NO: 38).

23. The nucleic acid of claim 17, wherein the antisense oligoribonucleotide comprises the RNA equivalent of at least nine nucleotides of ACCCGCAAAAT (SEQ ID NO: 38).

24. The nucleic acid of claim 17, wherein the antisense oligoribonucleotide comprises the RNA equivalent of ACCCGCAAAAT (SEQ ID NO: 38).

25. The nucleic acid of claim 17, wherein the antisense oligoribonucleotide is 15 to 30 nucleotides in length.

26. The nucleic acid of claim 17, wherein the antisense oligoribonucleotide is 20 to 40 nucleotides in length.

* * * * *

SEQUENCE LISTING ( 1 ) GENERAL INFORMATION:

( i i i ) NUMBER OF SEQUENCES: 49

( 2 ) INFORMATION FOR SEQ ID NO: 1:

( i ) SEQUENCE CHARACTERISTICS:
  ( A ) LENGTH: 40
  ( B ) TYPE: nucleic acid
  ( C ) STRANDEDNESS: single
  ( D ) TOPOLOGY: linear ( x i ) SEQUENCE DESCRIPTION: SEQ ID NO: 1:

GGAACCCACA CGTAGCGCAT CATTTTGCGG GTCACCATAT     40

( 2 ) INFORMATION FOR SEQ ID NO: 2:

( i ) SEQUENCE CHARACTERISTICS:
  ( A ) LENGTH: 35
  ( B ) TYPE: nucleic acid
  ( C ) STRANDEDNESS: single
  ( D ) TOPOLOGY: linear ( x i ) SEQUENCE DESCRIPTION: SEQ ID NO: 2:

AACCCACACG TAGCGCATCA TTTTGCGGGT CACCA     35

( 2 ) INFORMATION FOR SEQ ID NO: 3:

( i ) SEQUENCE CHARACTERISTICS:
  ( A ) LENGTH: 30
  ( B ) TYPE: nucleic acid
  ( C ) STRANDEDNESS: single
  ( D ) TOPOLOGY: linear ( x i ) SEQUENCE DESCRIPTION: SEQ ID NO: 3:

CCACACGTAG CGCATCATTT TGCGGGTCAC     30

( 2 ) INFORMATION FOR SEQ ID NO: 4:

( i ) SEQUENCE CHARACTERISTICS:
  ( A ) LENGTH: 30
  ( B ) TYPE: nucleic acid
  ( C ) STRANDEDNESS: single
  ( D ) TOPOLOGY: linear ( x i ) SEQUENCE DESCRIPTION: SEQ ID NO: 4:

GGAACCCACA CGTAGCGCAT CATTTTGCGG     30

( 2 ) INFORMATION FOR SEQ ID NO: 5:

( i ) SEQUENCE CHARACTERISTICS:
  ( A ) LENGTH: 27
  ( B ) TYPE: nucleic acid
  ( C ) STRANDEDNESS: single
  ( D ) TOPOLOGY: linear ( x i ) SEQUENCE DESCRIPTION: SEQ ID NO: 5:

CGTAGCGCAT CATTTTGCGG GTCACCA     27

( 2 ) INFORMATION FOR SEQ ID NO: 6:

( i ) SEQUENCE CHARACTERISTICS:
  ( A ) LENGTH: 25
  ( B ) TYPE: nucleic acid
  ( C ) STRANDEDNESS: single
  ( D ) TOPOLOGY: linear ( x i ) SEQUENCE DESCRIPTION: SEQ ID NO: 6:

ACACGTAGCG CATCATTTTG CGGGT                              25

( 2 ) INFORMATION FOR SEQ ID NO: 7:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 7:

CGTAGCGCAT CATTTTGCGG                                    20

( 2 ) INFORMATION FOR SEQ ID NO: 8:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( x i ) SEQUENCE DESCRIPTION: SEQ ID NO: 8:

TAGCGCATCA TTTTGC                                        16

( 2 ) INFORMATION FOR SEQ ID NO: 9:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO: 9:

CGCATCATTT TGCGGGTCAC CATAT                              25

( 2 ) INFORMATION FOR SEQ ID NO: 10:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO: 10:

CGCCTCATTT TGCGGGTCAC CATAT                              25

( 2 ) INFORMATION FOR SEQ ID NO: 11:

( i ) SEQUENCE CHARACTERISTICS:
        ( A ) LENGTH: 40
        ( B ) TYPE: nucleic acid
        ( C ) STRANDEDNESS: single
        ( D ) TOPOLOGY: linear ( x i ) SEQUENCE DESCRIPTION: SEQ ID NO: 11:

ATATGGTGAC CCGCAAAATG ATGCGCTACG TGTGGGTTCC              40

( 2 ) INFORMATION FOR SEQ ID NO: 12:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO: 12:

TGGTGACCCG CAAAATGATG CGCTACGTGT GGGTT                35

( 2 ) INFORMATION FOR SEQ ID NO: 13:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 13:

GTGACCCGCA AAATGATGCG CTACGTGTGG                30

( 2 ) INFORMATION FOR SEQ ID NO: 14:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 14:

ATATGGTGAC CCGCAAAATG ATGCGCTACG                30

( 2 ) INFORMATION FOR SEQ ID NO: 15:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 15:

CCGCAAAATG ATGCGCTACG TGTGGGTTCC                30

( 2 ) INFORMATION FOR SEQ ID NO: 16:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO: 16:

ACCCGCAAAA TGATGCGCTA CGTGT                25

( 2 ) INFORMATION FOR SEQ ID NO: 17:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 17:

CCGCAAAATG ATGCGCTACG                20

( 2 ) INFORMATION FOR SEQ ID NO: 18:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 18:

ATATGGTGAC CCGCAAAATG                20

( 2 ) INFORMATION FOR SEQ ID NO: 19:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 19:

ATGCGCTACG TGTGGGTTCC 20

( 2 ) INFORMATION FOR SEQ ID NO: 20:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( x i ) SEQUENCE DESCRIPTION: SEQ ID NO: 20:

GCAAAATGAT GCGCTA 16

( 2 ) INFORMATION FOR SEQ ID NO: 21:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( x i ) SEQUENCE DESCRIPTION: SEQ ID NO: 21:

ATATGGTGAC CCGCAA 16

( 2 ) INFORMATION FOR SEQ ID NO: 22:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( x i ) SEQUENCE DESCRIPTION: SEQ ID NO: 22:

GCTACGTGTG GGTTCC 16

( 2 ) INFORMATION FOR SEQ ID NO: 23:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO: 23:

ATATGGTGAC CCGCAAAATG AGGCG 25

( 2 ) INFORMATION FOR SEQ ID NO: 24:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( x i ) SEQUENCE DESCRIPTION: SEQ ID NO: 24:

CCGAGCTCCA CCAATCGGCA GTCAGGAAG 29

( 2 ) INFORMATION FOR SEQ ID NO: 25:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( x i ) SEQUENCE DESCRIPTION: SEQ ID NO: 25:

| CGATCGATTC AGCGCCGACG GACGTA | 26 |
|---|---|

( 2 ) INFORMATION FOR SEQ ID NO: 26:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 26:

| CAGAATTCAA GCCTCCAAGC TGTGCCTTGG | 30 |
|---|---|

( 2 ) INFORMATION FOR SEQ ID NO: 27:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 27:

| AGTCTAGACT CTGCGGTATT GTGAGGATTC TTG | 33 |
|---|---|

( 2 ) INFORMATION FOR SEQ ID NO: 28:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( x i ) SEQUENCE DESCRIPTION: SEQ ID NO: 28:

| CGGAGCTCCT AGCCGCTTGT TTTGCTCGCA GC | 32 |
|---|---|

( 2 ) INFORMATION FOR SEQ ID NO: 29:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO: 29:

| GAAAGCTTCT GCGACGCGGC GATTGAGA | 28 |
|---|---|

( 2 ) INFORMATION FOR SEQ ID NO: 30:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear ( x i ) SEQUENCE DESCRIPTION: SEQ ID NO: 30:

| GAGGGAAACC ACACGTAGCG CATCATTTTG CGGGT | 35 |
|---|---|

( 2 ) INFORMATION FOR SEQ ID NO: 31:

( i ) SEQUENCE CHARACTERISTICS:
    ( A ) LENGTH: 35
    ( B ) TYPE: nucleic acid
    ( C ) STRANDEDNESS: single
    ( D ) TOPOLOGY: linear ( x i ) SEQUENCE DESCRIPTION: SEQ ID NO: 31:

GAGGGAACCC ACACGTAGCG CATCATTTTC CGGGT     35

( 2 ) INFORMATION FOR SEQ ID NO: 32:

( i ) SEQUENCE CHARACTERISTICS:
    ( A ) LENGTH: 40
    ( B ) TYPE: nucleic acid
    ( C ) STRANDEDNESS: single
    ( D ) TOPOLOGY: linear ( x i ) SEQUENCE DESCRIPTION: SEQ ID NO: 32:

ATATGGTGAC CCGGAAAATG ATGCGCTACG TGTGGTTTCC     40

( 2 ) INFORMATION FOR SEQ ID NO: 33:

( i ) SEQUENCE CHARACTERISTICS:
    ( A ) LENGTH: 25
    ( B ) TYPE: nucleic acid
    ( C ) STRANDEDNESS: single
    ( D ) TOPOLOGY: linear ( x i ) SEQUENCE DESCRIPTION: SEQ ID NO: 33:

GAGCTCCTGA TAACCGGAGT AAGGA     25

( 2 ) INFORMATION FOR SEQ ID NO: 34:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( x i ) SEQUENCE DESCRIPTION: SEQ ID NO: 34:

TGTTCCCAAG AATATGGT     18

( 2 ) INFORMATION FOR SEQ ID NO: 35:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( x i ) SEQUENCE DESCRIPTION: SEQ ID NO: 35:

GCATCATTAT AATTCGGG     18

( 2 ) INFORMATION FOR SEQ ID NO: 36:

( i ) SEQUENCE CHARACTERISTICS:
    ( A ) LENGTH: 23
    ( B ) TYPE: nucleic acid
    ( C ) STRANDEDNESS: single
    ( D ) TOPOLOGY: linear ( x i ) SEQUENCE DESCRIPTION: SEQ ID NO: 36:

TGTTCCCAAG AATATGGTGA CCC     23

( 2 ) INFORMATION FOR SEQ ID NO: 37:

( i ) SEQUENCE CHARACTERISTICS:
    ( A ) LENGTH: 23

(B) TYPE: nucleic acid
        (C) STRANDEDNESS: single
        (D) TOPOLOGY: linear (xi) SEQUENCE DESCRIPTION: SEQ ID NO: 37:

TACGCAGCAG ACCCTTAGTC GTA                                                                        23

(2) INFORMATION FOR SEQ ID NO: 38:

(i) SEQUENCE CHARACTERISTICS:
        (A) LENGTH: 11
        (B) TYPE: nucleic acid
        (C) STRANDEDNESS: single
        (D) TOPOLOGY: linear (xi) SEQUENCE DESCRIPTION: SEQ ID NO: 38:

ATTTTGCGGG T                                                                                     11

(2) INFORMATION FOR SEQ ID NO: 39:

(i) SEQUENCE CHARACTERISTICS:
        (A) LENGTH: 13
        (B) TYPE: nucleic acid
        (C) STRANDEDNESS: single
        (D) TOPOLOGY: linear (xi) SEQUENCE DESCRIPTION: SEQ ID NO: 39:

TNATTTTGCG GGT                                                                                   13

(2) INFORMATION FOR SEQ ID NO: 40:

(i) SEQUENCE CHARACTERISTICS:
        (A) LENGTH: 11
        (B) TYPE: nucleic acid
        (C) STRANDEDNESS: single
        (D) TOPOLOGY: linear (xi) SEQUENCE DESCRIPTION: SEQ ID NO: 40:

ACCCGCAAAA T                                                                                     11

(2) INFORMATION FOR SEQ ID NO: 41:

(i) SEQUENCE CHARACTERISTICS:
        (A) LENGTH: 13
        (B) TYPE: nucleic acid
        (C) STRANDEDNESS: single
        (D) TOPOLOGY: linear (xi) SEQUENCE DESCRIPTION: SEQ ID NO: 41:

ACCCGCAAAA TNA                                                                                   13

(2) INFORMATION FOR SEQ ID NO: 42:

(i) SEQUENCE CHARACTERISTICS:
        (A) LENGTH: 40
        (B) TYPE: nucleic acid
        (C) STRANDEDNESS: single
        (D) TOPOLOGY: linear (xi) SEQUENCE DESCRIPTION: SEQ ID NO: 42:

GGAACCCACA CGTAGCGCAT CATTTGCGG GTCACCATAT                                                        40

(2) INFORMATION FOR SEQ ID NO: 43:

(i) SEQUENCE CHARACTERISTICS:
        (A) LENGTH: 16
        (B) TYPE: nucleic acid
        (C) STRANDEDNESS: single ( D ) TOPOLOGY: linear ( x i ) SEQUENCE DESCRIPTION: SEQ ID NO: 43:

TAGCGCATCA TTTTGC   16

( 2 ) INFORMATION FOR SEQ ID NO: 44:

( i ) SEQUENCE CHARACTERISTICS:
        ( A ) LENGTH: 40
        ( B ) TYPE: nucleic acid
        ( C ) STRANDEDNESS: single
        ( D ) TOPOLOGY: linear ( x i ) SEQUENCE DESCRIPTION: SEQ ID NO: 44:

ATATGGTGAC CCGCAAAATG ATGCGCTACG TGTGGGTTCC   40

( 2 ) INFORMATION FOR SEQ ID NO: 45:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 45:

TTCAAGCCTC CAAGCTGTGC CTTGGGTGGC   30

( 2 ) INFORMATION FOR SEQ ID NO: 46:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 46:

GCCACCCAAG GCACAGCTTG GAGGCTTGAA   30

( 2 ) INFORMATION FOR SEQ ID NO: 47:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 47:

TACGTCCCGT CGGCGCTGAA TCCCGCGGAC   30

( 2 ) INFORMATION FOR SEQ ID NO: 48:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 48:

GTCCGCGGGA TTCAGCGCCG ACGGGACGTA   30

( 2 ) INFORMATION FOR SEQ ID NO: 49:

( i ) SEQUENCE CHARACTERISTICS:
        ( A ) LENGTH: 816
        ( B ) TYPE: nucleic acid
        ( C ) STRANDEDNESS: single
        ( D ) TOPOLOGY: linear (x i) SEQUENCE DESCRIPTION: SEQ ID NO: 49:

```
CGGGACCGAG GCAGGTCCCC TAGAAGAAGA ACTCCCTCGC CTCGCAGACG CAGATCTCCA    60
TCGCCGCGTC GCAGAAGATC TCAATCTCGG GAATCTCAAT GTTAGTATTC CTTGGACTCA   120
TAAGGTGGGA AACTTTACGG GGCTTTATTC CTCTACAGTA CCTATCTTTA ATCCTGAATG   180
GCAAACTCCT TCCTTTCCTA AGATTCATTT ACAAGAGGAC ATTATTAATA GGTGTCAACA   240
ATTTGTGGGC CCTCTCACTG TAAATGAAAA GAGAAGATTG AAATTAATTA TGCCTGCTAG   300
ATTCTATCCT ACCCACACTA AATATTTGCC CTTAGACAAA GGAATTAAAC CTTATTATCC   360
AGATCAGGTA GTTAATCATT ACTTCCAAAC CAGACATTAT TTACATACTC TTTGGAAGGC   420
TGGTATTCTA TATAAGCGGG AAACCACACG TAGCGCATCA TTTTGCGGGT CACCATATTC   480
TTGGAACAA  GAGCTACAGC ATGGGAGGTT GGTCATCAAA ACCTCGCAAA GGCATGGGGA   540
CGAATCTTTC TGTTCCCAAT CCTCTGGGAT TCTTTCCCGA TCATCAGTTG GACCCTGCAT   600
TCGGAGCCAA CTCAAACAAT CCAGATTGGG ACTTCAACCC CGTCAAGGAC GACTGGCCAG   660
CAGCCAACCA AGTAGGAGTG GGAGCATTCG GGCCAAGGCT CACCCCTCCA CACGGCGGTA   720
TTTTGGGGTG GAGCCCTCAG GCTCAGGGCA TATTGACCAC AGTGTCAACA ATTCCTCCTC   780
CTGCCTCCAC CAATCGGCAG TCAGGAAGGC AGCCTA                             816
```